(12) United States Patent
Krueger

(10) Patent No.: US 12,383,178 B2
(45) Date of Patent: *Aug. 12, 2025

(54) SYSTEMS AND METHODS FOR USING EYE IMAGING ON A WEARABLE DEVICE TO ASSESS HUMAN HEALTH

(71) Applicant: Wesley W. O. Krueger, San Antonio, TX (US)

(72) Inventor: Wesley W. O. Krueger, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/749,585

(22) Filed: Jun. 20, 2024

(65) Prior Publication Data

US 2024/0350051 A1    Oct. 24, 2024

Related U.S. Application Data

(63) Continuation-in-part of application No. 18/406,199, filed on Jan. 7, 2024, now Pat. No. 12,133,567, which is a continuation-in-part of application No. 17/989,429, filed on Nov. 17, 2022, now Pat. No. 12,042,294, which is a continuation-in-part of application No. 17/576,673, filed on Jan. 14, 2022, now Pat. No. 11,504,051, which is a continuation-in-part of application No. 16/903,136, filed on Jun. 16, 2020, now Pat. No. 11,490,809, which is a continuation-in-part of application No. 16/264,242, filed on Jan. 31, 2019, now Pat. No. 10,716,469, which is a continuation-in-part of
(Continued)

(51) Int. Cl.
*A61B 5/16* (2006.01)
*A61B 5/00* (2006.01)
*G16H 50/30* (2018.01)

(52) U.S. Cl.
CPC .............. *A61B 5/163* (2017.08); *A61B 5/165* (2013.01); *A61B 5/4064* (2013.01); *A61B 5/4088* (2013.01); *A61B 5/4866* (2013.01); *A61B 5/6803* (2013.01); *G16H 50/30* (2018.01)

(58) Field of Classification Search
CPC ....... A61B 5/163; A61B 5/165; A61B 5/4064; A61B 5/4088; A61B 5/4866; A61B 5/6803; G16H 50/30
USPC ........................................................ 600/558
See application file for complete search history.

(56) References Cited

U.S. PATENT DOCUMENTS 3,616,463 A    11/1971   Theodore et al.
4,817,633 A    4/1989    McStravick et al.
(Continued)

FOREIGN PATENT DOCUMENTS

WO    2013117727    8/2013

OTHER PUBLICATIONS

Allison et al. Combined Head and Eye Tracking System for Dynamic Testing of the Vestibular System. IEEE Transactions on Biomedical Engineering. vol. 43 No. 11, Nov. 1996 (USA).

*Primary Examiner* — Mohammed A Hasan

(57) ABSTRACT

A system for assessing human health that comprises a wearable device, such as a virtual reality device, an augmented reality device, or a mixed reality device. The wearable device comprises an eye imaging module and a display. The eye imaging module is configured for imaging an eye component at a plurality of times. An electronic circuit is responsive to the eye imaging information to generate an ocular parameter measurement. The ocular parameter measurement is used to determine a human health condition.

20 Claims, 14 Drawing Sheets

Related U.S. Application Data application No. 15/713,418, filed on Sep. 22, 2017, now Pat. No. 10,231,614, which is a continuation-in-part of application No. 15/162,300, filed on May 23, 2016, now Pat. No. 9,788,714, which is a continuation-in-part of application No. 14/326,335, filed on Jul. 8, 2014, now Pat. No. 9,370,302, said application No. 17/576,673 is a continuation-in-part of application No. 16/805,253, filed on Feb. 28, 2020, now Pat. No. 11,389,059, which is a continuation-in-part of application No. 16/351,326, filed on Mar. 12, 2019, now Pat. No. 10,602,927, which is a continuation-in-part of application No. 16/264,242, filed on Jan. 31, 2019, now Pat. No. 10,716,469, which is a continuation-in-part of application No. 13/749,873, filed on Jan. 25, 2013, now abandoned.

(56) References Cited

U.S. PATENT DOCUMENTS

| | | |
|---|---|---|
| 5,180,907 A | 1/1993 | Udden et al. |
| 5,204,998 A | 4/1993 | Liu |
| 5,550,601 A | 8/1996 | Donaldson |
| 5,555,895 A | 9/1996 | Ulmer et al. |
| 5,621,922 A | 4/1997 | Russ |
| 5,838,420 A | 11/1998 | Donaldson et al. |
| 5,919,149 A | 7/1999 | Allum |
| 5,942,954 A | 8/1999 | Galiana et al. |
| 5,953,102 A | 9/1999 | Berry |
| 5,978,972 A | 11/1999 | Steward et al. |
| 6,301,718 B1 | 10/2001 | Rigal |
| 6,796,947 B2 | 9/2004 | Watt et al. |
| 6,826,509 B2 | 11/2004 | Crisco et al. |
| 6,931,671 B2 | 8/2005 | Skiba |
| 7,276,458 B2 | 10/2007 | Wen |
| 7,380,938 B2 | 6/2008 | Chmielewski et al. |
| 7,386,401 B2 | 6/2008 | Vock et al. |
| 7,401,920 B1 | 7/2008 | Kranz et al. |
| 7,448,751 B2 | 11/2008 | Kiderman et al. |
| 7,500,752 B2 | 3/2009 | Nashner |
| 7,509,835 B2 | 3/2009 | Beck |
| 7,526,389 B2 | 4/2009 | Greenwald et al. |
| 7,651,224 B2 | 1/2010 | Wood et al. |
| 7,682,024 B2 | 3/2010 | Plant et al. |
| 7,727,162 B2 | 6/2010 | Peterka |
| 7,731,360 B2 | 6/2010 | MacDougall et al. |
| 7,753,523 B2 | 7/2010 | Kiderman et al. |
| 7,849,524 B1 | 12/2010 | Williamson et al. |
| 7,866,818 B2 | 1/2011 | Schroeder et al. |
| 7,931,370 B2 | 4/2011 | Bartomeu |
| 7,988,287 B1 | 8/2011 | Butler et al. |
| 8,232,881 B2 | 7/2012 | Hertz |
| 8,253,814 B2 | 8/2012 | Zhang et al. |
| 8,285,416 B2 | 10/2012 | Cho et al. |
| 8,510,166 B2 | 8/2013 | Neven |
| 8,529,463 B2 | 9/2013 | Della Santina et al. |
| 8,578,520 B2 | 11/2013 | Halldin |
| 8,696,126 B2 | 4/2014 | Yoo et al. |
| 8,764,193 B2 | 7/2014 | Kiderman et al. |
| 10,191,294 B2 | 1/2019 | Macnamara |
| 10,535,151 B2 | 1/2020 | Bleyer et al. |
| 12,133,567 B2 * | 11/2024 | Krueger ............... G16H 10/60 |
| 2002/0118339 A1 | 8/2002 | Lowe |
| 2002/0176051 A1 * | 11/2002 | Saladin ............... A61B 3/032 |
| | | 351/239 |
| 2006/0059606 A1 | 3/2006 | Ferrara |
| 2006/0098087 A1 | 5/2006 | Brandt et al. |
| 2006/0270945 A1 | 11/2006 | Ghajar |
| 2008/0022441 A1 | 1/2008 | Oranchak et al. |
| 2009/0021695 A1 | 1/2009 | Scarpino |
| 2010/0036289 A1 | 2/2010 | White et al. |
| 2010/0092049 A1 | 4/2010 | Schroeder et al. |
| 2010/0101005 A1 | 4/2010 | Cripton et al. |
| 2010/0198104 A1 | 8/2010 | Schubert et al. |
| 2010/0280372 A1 | 11/2010 | Poolman et al. |
| 2011/0176106 A1 | 7/2011 | Lewkowski |
| 2011/0209272 A1 | 9/2011 | Drake |
| 2012/0133892 A1 | 5/2012 | Furman et al. |
| 2012/0143526 A1 | 6/2012 | Benzel et al. |
| 2012/0194551 A1 * | 8/2012 | Osterhout ............ G06F 3/005 |
| | | 345/633 |
| 2012/0198604 A1 | 8/2012 | Weber et al. |
| 2012/0204327 A1 | 8/2012 | Faden et al. |
| 2012/0297526 A1 | 11/2012 | Leon |
| 2013/0232668 A1 | 9/2013 | Suddaby |
| 2013/0278899 A1 | 10/2013 | Waldorf et al. |
| 2014/0111771 A1 | 4/2014 | Liu |
| 2014/0171756 A1 | 6/2014 | Waldorf et al. |
| 2014/0192326 A1 | 7/2014 | Kiderman et al. |
| 2014/0327880 A1 | 11/2014 | Kiderman et al. |
| 2015/0038803 A1 | 2/2015 | Uhlig et al. |
| 2015/0051508 A1 | 2/2015 | Ghajar et al. |
| 2015/0223683 A1 | 8/2015 | Davidovics et al. |
| 2015/0243099 A1 | 8/2015 | Schowengerdt |
| 2015/0245766 A1 | 9/2015 | Rennaker et al. |
| 2015/0335239 A1 | 11/2015 | MacDougall |
| 2016/0033750 A1 | 2/2016 | Nunnink et al. |
| 2016/0062459 A1 | 3/2016 | Publicover et al. |
| 2016/0081546 A1 | 3/2016 | MacDougall |
| 2016/0085302 A1 | 3/2016 | Publicover et al. |
| 2016/0106315 A1 | 4/2016 | Kempinski |
| 2016/0110920 A1 | 4/2016 | Schowengerdt |
| 2016/0132726 A1 | 5/2016 | Kempinski et al. |

* cited by examiner

SYSTEMS AND METHODS FOR USING EYE IMAGING ON A WEARABLE DEVICE TO ASSESS HUMAN HEALTH

CROSS REFERENCE TO RELATED APPLICATIONS

This application is a continuation-in-part of U.S. patent application Ser. No. 18/406,199 filed 7 Jan. 2024, which is a continuation-in-part of U.S. patent application Ser. No. 17/989,429 filed 17 Nov. 2022, which is a continuation-in-part of U.S. patent application Ser. No. 17/576,673, filed 14 Jan. 2022, now U.S. Pat. No. 11,504,051, which is a continuation-in-part of U.S. patent application Ser. No. 16/903,136 filed 16 Jun. 2020, now U.S. Pat. No. 11,490,809, which is a continuation-in-part of U.S. patent application Ser. No. 16/264,242 filed 31 Jan. 2019, now U.S. Pat. No. 10,716,469, which is a continuation-in-part of U.S. patent application Ser. No. 15/713,418 filed 22 Sep. 2017, now U.S. Pat. No. 10,231,614, which is a continuation-in-part of U.S. patent application Ser. No. 15/162,300 filed 23 May 2016, now U.S. Pat. No. 9,788,714, which is a continuation-in-part of U.S. patent application Ser. No. 14/326,335 filed 8 Jul. 2015, now U.S. Pat. No. 9,370,302 filed 8 Jul. 2014. U.S. patent application Ser. No. 16/264,242 is also a continuation-in-part of U.S. patent application Ser. No. 13/749,873 filed 25 Jan. 2013. The entire disclosures of all aforementioned documents are incorporated by reference herein.

FIELD OF INVENTION

Embodiments of the invention(s) herein relate to a wearable device for observing eye position, eye motion, pupil size, and/or eyeblinks in response to visual information displayed on the device. The display on the device can be a virtual reality (VR) display, an augmented reality (AR) display, or a mixed reality (MR) display, collectively defined as extended reality (XR). Embodiments can use the eye observations to measure ocular parameters such as saccades, vergence, head static smooth pursuit, vestibular ocular reflex (VOR), vestibular ocular reflex suppression (VORS), eye fixation and/or gaze, pupil size changes, and/or eyeblinks, which in turn can be used to determine:
  (a) performance for individuals with normal human health;
  (b) neurologic conditions, such as traumatic brain injury;
  (c) mental health conditions, such as cognitive impairment;
  (d) biochemical health impairments, such as metabolic dysfunction;
  (e) physiologic health impairments, such as fatigue; and/or
  (f) behavioral health conditions, such as substance use impairment.

BACKGROUND

The eyes and eye responses are often considered a window for assessing central nervous system function. Eye tracking can have significant value in assessing neurologic conditions, mental health conditions, behavioral health conditions, physiologic impairments, and biochemical impairments. Eye tracking can measure biomarkers for these human health conditions, disorders, or impairments. Eye tracking can improve safety in sports, the workplace, and law enforcement. It can assess disabilities in medicine, rehabilitation, and legal environments. It can determine pharmaceutical efficacy with some drugs. Eye tracking can enable early treatments to prevent symptoms and functional disabilities. It can control the safe operation of vehicles. Extended reality (XR) devices can be combined with eye tracking, to improve a health diagnosis, especially outside of a clinical environment.

There are reportedly 3.8 million sports-related concussions (also known as traumatic brain injuries or TBIs) annually in the U.S., more than half of which are unreported. There may be no one to notice, no resources to properly evaluate, or the individual might not report the event. Current methods of assessment for suspected concussions are inadequate. An average football player experiences about 378 head impacts per season. Secondary concussions pose an even greater risk, particularly if timed close to a previous concussion. Younger players at a greater risk of permanent brain injury from concussions. There are over 250,000 emergency room visits of young individuals annually for sports and recreation related head injuries. Over 50 million Americans participate in team sports, all of whom are at risk of concussions. Concussions from multiple head impacts can result in chronic traumatic encephalopathy (CTE), which often is associated with behavioral health impairments and has caused many professional players to commit suicides. Central nervous system (CNS) impairments can persist in individuals with TBIs long after the last episode. Even a mild TBI (mTBI), can cause oculomotor abnormalities and visual problems. It has been demonstrated that neurologic conditions, such as TBSs, can produce measurable changes in: saccades, head static smooth pursuit, vestibular ocular reflex (VOR), vestibular ocular reflex suppression (VORS), vergence, eye fixation, and/or pupil size changes.

It has been estimated that 1 in 4 individuals will experience a mental health condition at some point in their lives. A significant number of military personnel may experience mental health issues during or after deployment. Approximately 14% to 16% of the US service members deployed to Afghanistan and Iraq had PTSD or depression. Athletes are commonly affected with mental health conditions. 60-65% of high school and college athletes suffer anxiety and stress. The demands and pressures of sports, and the physical and emotional toll of training and competition, contribute to this issue. Common mental health conditions experienced by athletes include depression, anxiety, attention deficit hyperactivity disorder (ADHD), and cognitive disorders. The unique stressors and demands of sports can sometimes exacerbate or trigger these conditions. Abnormalities of saccades, eye fixation, duration of eye fixation, blink rate, head static smooth pursuit, VOR, and VORS have been associated with mental health conditions as well as disturbances of visual attention, visual navigation, visual perception, visual search and visual reasoning.

Behavioral health conditions often manifest as deviant social behaviors or interfere with daily life. Behavior health conditions can be characterized by substance abuse (e.g., alcohol, drugs), which can affect jobs/play activity, safety, health, and liability.

Biochemical impairments are common, resulting in metabolic dysfunction such as diabetes, enzymatic deficiencies such as lactose intolerance, hormone abnormalities such as thyroid dysfunction or diabetes mellitus, nutritional deficiencies such as iron deficiency. It has also been documented that biochemical health impairments caused by metabolic dysfunctions (dehydration, renal failure, and diabetes), and pulmonary impairments (hypercapnia or hypoxia), can cause changes in: saccades, head static smooth pursuit, VOR, VORS, vergence, pupil size changes, eye fixation, and/or eyeblinks.

Physiological health impairments are common in civilian and military populations. For example, there is a reported incidence of 40% to over 80% in athletes. This results in physical and cognitive performances impairments, and increased injuries. Additionally, it has been demonstrated that physiologic health impairments such as fatigue can cause measurable changes in one or more of the following ocular parameters: pupil size changes, saccades, eye fixation, and head static smooth pursuit and vestibular ocular reflex suppression.

Measures of eye movements, eye responses, eye positions and/or eye components (such as pupil size changes and eyeblinks) can be used to assess each of the health conditions accurately. Each of the aforementioned human health conditions can affect different areas of the neurologic system and each of the ocular parameters to be measured can assess different anatomical regions and neural pathways of the brain. Human health conditions and certain health disorders or impairments may be more accurately assessed by different ocular parameter measurements or by using a combination of ocular parameter measurements.

Historically, human health was assessed in a clinical setting. New sensors and electronic technologies enable the use of portable systems for non-clinical environments. Such advancements facilitate increases in speed and accuracy for eye position and movement observations to measure ocular parameters such as saccades, vergence, head static smooth pursuit, vestibular ocular reflex (VOR), vestibular ocular reflex suppression (VORS), gaze, eye fixation, pupil size and/or eyeblinks.

It is desired to overcome limitations of the prior art by using eye-observation and wearable extended reality (XR) systems/methods to assess human health to:
 a. Assess human ocular parameters;
 b. Determine human health conditions, disorders, or impairment;
 c. Determine biomarkers for human health conditions;
 d. Use eye data information for health condition intervention;
 e. Measure gaze and eye fixation ability;
 f. Incorporate artificial intelligence and machine learning in assessing human health;
 g. Determine rehabilitation need and/or training and monitor efficacy during activity;
 h. Generate the protocol needed for rehabilitation and/or training;
 i. Provide training and rehabilitation in response to collected eye data;
 j. Determine pharmaceutical need for intervention and treatment efficacy;
 k. Enable early treatments to prevent symptoms and functional disabilities;
 l. Use eye data as input control of a system;
 m. Transmit eye recorded data regarding health status remotely;
 n. Use abnormal eye information detected to control a vehicle;
 o. Improve health safety in activities;
 p. Assess health impairment in multiple environment including medicine, sports, commercial rehabilitation, law, and legal environments;
 q. Capture high frequency eye movements (such as microsaccades);
 r. Detect abnormalities in real time and on/in the location of user activity.

Potential benefits of the eye tracking devices that incorporate extended reality (XR) technology, can provide changes in the standards of care and clinical recommendations by optimizing rapid evaluation and treatment. Ocular parameter measurements can be used to assess different areas of the central nervous system and different human health factors. Such systems and methods can function as health care provider extenders by detecting abnormalities, monitoring recovery, and establishing rehabilitation programs. Such technologies can detect abnormalities or impairments, define the characteristics of the disorder, quantify the deficit, and wirelessly transmit this information remotely. If an abnormal ocular parameter is noted, rehabilitation can begin earlier and decisions regarding the need for returning to play or a previous work activity can be determined.

BRIEF DESCRIPTION OF THE DRAWINGS

The present invention will be better understood on reading the following detailed description of non-limiting embodiments thereof, and on examining the accompanying drawings, in which.

Figure 1:
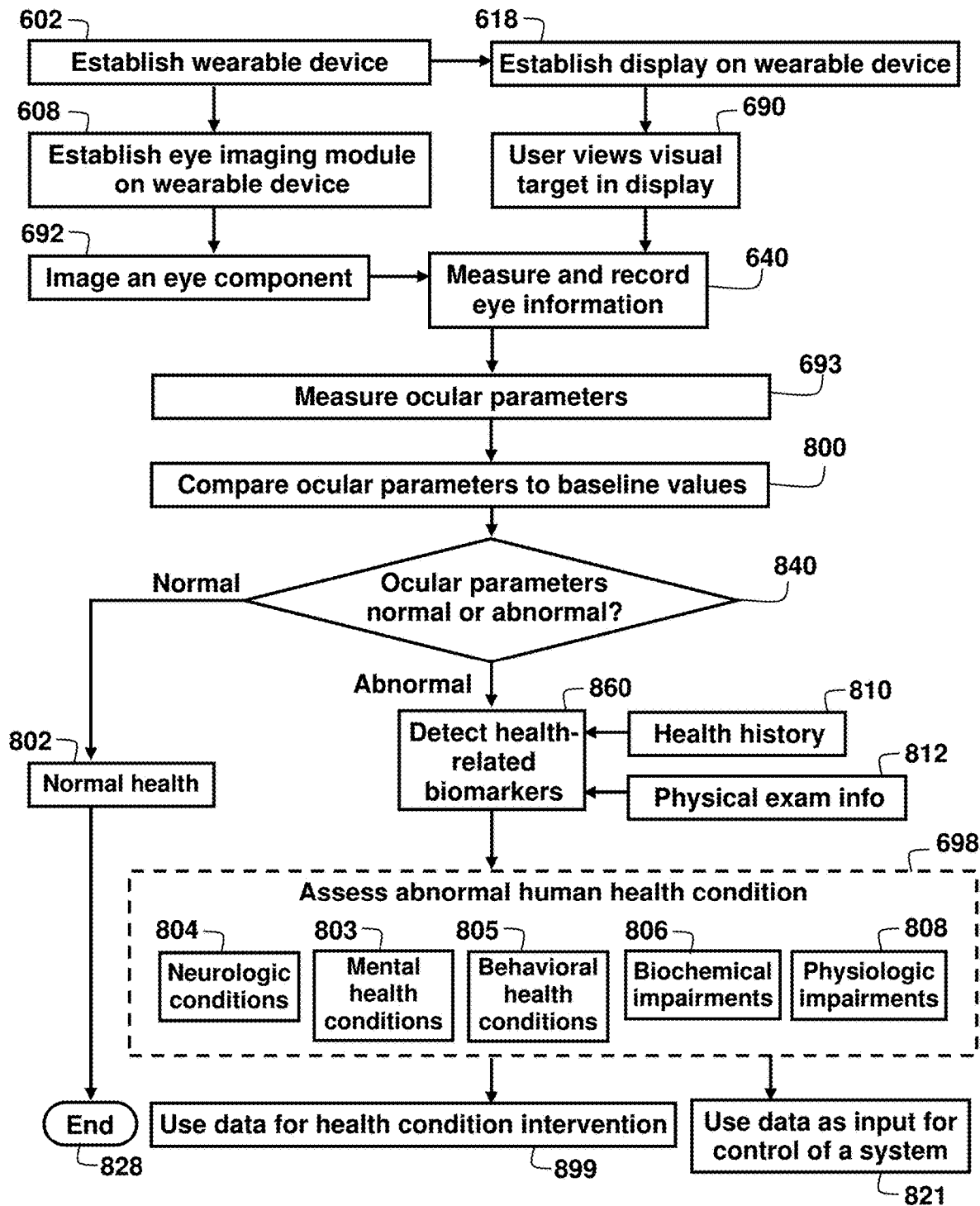
FIG. 1 is a method for using eye imaging on an extended reality device to assess health.

It should be understood that the drawings are not necessarily to scale. In certain instances, details that are not necessary for an understanding of the invention or that render other details difficult to perceive may have been omitted. It should be also understood that the invention is not necessarily limited to the embodiments illustrated herein.

DETAILED DESCRIPTION

The ensuing description provides preferred exemplary embodiment(s) only, and is not intended to limit the scope, applicability, or configuration of the disclosure. Rather, the ensuing description of the preferred exemplary embodiment(s) will provide those skilled in the art with an enabling description for implementing preferred exemplary embodiment(s). It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details.

In one embodiment, the present invention uses at least one eye imaging sensor located on an extended reality (XR) device to assess human health during an activity subject to head trauma or other hazards. The eye imaging sensor or sensors could measure eye movement (such as saccades), eye position, pupil size, eyeblinks, and/or other eye information in individuals participating in sports or other activities. The human health condition being assessed could be a neurologic condition, a mental health condition, a behavioral health condition, a biochemical impairment, a physiologic impairment, or normal health.

Abnormal human health conditions that can be assessed using ocular parameters include neurologic conditions, mental health conditions, behavioral health conditions, biochemical impairments, and physiologic impairments. The following table lists examples of types of human health conditions, and related ocular parameters that can be measured. Each of these impairments can affect different areas of the central nervous system.

| Human health condition | Underlying health cause | Measured eye parameters |
| --- | --- | --- |
| Traumatic brain injury (TBI, commonly rereferred to as a concussion) | Blunt trauma concussion<br>Blast concussion<br>Diffuse axonal injury | Eye fixation, Pupil size<br>Head static smooth pursuit<br>VOR, VORS<br>Saccades, Vergence |
| Neurocognitive impariments | Alzheimer's, Parkinson's<br>Lewy Body Dementia<br>Frontotemporal impairments<br>Neuroviral impairments | Eye fixation<br>Head static smooth pursuit<br>Pupil size changes<br>Saccades |
| Cerebral inflammatory or autoimmune impairments | Multiple sclerosis<br>Guillain-Barré syndrome<br>Encephalitis, Meningitis | Head static smooth pursuit<br>Saccades<br>Vergence |
| Cerebrovascular (CV) impairments | Migraines, Stroke<br>Transient ischemic attack (TIA)<br>Vascular dementia<br>CV stenosis, CV aneurysms | Head static smooth pursuit<br>VOR, VORS<br>Pupil size changes<br>Saccades |
| Seizure impairments | Focal seizures<br>Generalized seizures | Eyeblinks |
| Neuromuscular impairments | Muscular dystrophy<br>Myasthenia gravis<br>Cerebral palsy<br>Dystonia | Eyeblinks<br>Head static smooth pursuit |
| Neurogenetic impairments | Tay-Sachs disease<br>Neurofibromatosis | Head static smooth pursuit<br>Eye fixation |
| Neurodegenerative impairments | Amyotrophic Lateral Sclerosis<br>Huntington's disease<br>Spinocerebellar Ataxia | Head static smooth pursuit<br>Eye fixation<br>Saccades |
| Neoplastic impairments | Brain tumors | Vergence<br>Head static smooth pursuit<br>Saccades<br>Eye fixation |

The following table lists types of mental health conditions, examples, and related ocular parameters that can be measured.

| Human health condition | Underlying health cause | Measured eye parameters |
| --- | --- | --- |
| Mental health condition | Cognitive impairment | Head static smooth pursuit<br>Pupil size changes<br>Saccades, Eyeblinks |
| Mental health condition | Chronic traumatic encephalopathy (CTE) | Eye fixation<br>Head static smooth pursuit<br>Saccades |
| Mental health condition | Attention deficit hyperactivity disorder (ADHD) | Eye fixation<br>Head static smooth pursuit<br>Saccades<br>Vergence |
| Mental health condition | Anxiety disorder | Head static smooth pursuit<br>VORS<br>Saccades, Eyeblinks |
| Mental health condition | Depression | Eyeblinks<br>Eye fixation<br>VORS<br>Pupil size changes |

The following table lists types of behavioral health conditions, biochemical health impairments, and physiologic health impairments and related ocular parameters.

| Human health condition | Underlying health cause | Measured eye parameters |
|---|---|---|
| Mental health condition | Depression | Eyeblinks<br>Eye fixation<br>VORS<br>Pupil size changes |
| Behavioral health condition | Mood or Emotion | Saccades<br>Eyeblinks<br>Eye fixation<br>Pupil size changes |
| Behavioral health condition | Substance use impairment | Saccades<br>Head static smooth pursuit<br>VOR, VORS<br>Pupil size changes |
| Biochemical health impairment | Metabolic or hormonal abnormalities (diabetes, etc) | Head static smooth pursuit<br>Pupil size changes<br>Saccades, Eyeblinks |
| Biochemical health impairment | Pulmonary impairments such as increased $CO_2$ or decreased $O_2$ | Pupil size changes<br>Vergence<br>Saccades, Eyeblinks |
| Physiologic health impairment | Fatigue/lack of alertness | Eye fixation<br>Pupil size changes<br>Saccades, Eyeblinks |
| Physiologic health impairment | Spatial disorientation | Eye fixation<br>VOR, VORS<br>Saccades |
| Physiologic health impairment | Intracranial pressure impairments within the skull | Eye fixation<br>Pupil size changes<br>Saccades, Vergence |
| Physiologic health impairment | Dizziness related to labyrinthine impairments | Head static smooth pursuit<br>VOR, VORS<br>Saccades, Vergence |

As shown in the preceding tables, different human health conditions require different ocular parameter measurements to detect an abnormality. The ocular parameter being tested must involve the neurologic pathway which was affected by the impairment. Additionally, certain health conditions have characteristic ocular parameter abnormalities. Examples are:

a. Many mental health conditions such as attention deficit hyperactivity disorder (ADHD) have demonstrated abnormal saccades, impairments with smooth pursuit, eye fixation and vergence. These impairments with eye movement can be associated with poor reading skills.

b. While neuropsychological testing traditionally has been used to measure mental health performance and mental processing deficits, the cerebral influences on the ocular motor system provide another quantitative mental health deficit assessment method. Abnormal eye movements can precede detection of mental conditions before neuropsychological cognitive testing and can accurately assess different mental domains. Different mental health conditions can be readily apparent with abnormalities of saccades, head static smooth pursuit, vestibular ocular reflex suppression (VORS), vergence, eye fixation, and pupil size changes when measuring ocular parameters.

c. Biochemical impairments of hormones, electrolytes, metabolites, and gases can result in abnormal eye movements. For example, high cortisol can be the trigger for adrenal stress symptoms and related long-term health problems. Cortisol levels have a profound effect on our eyes and vision. Some of the symptoms that can occur include double vision, sensitivity to bright light, difficulty focusing up close, memory issues, and blurred vision. Loss of sodium and dehydration can lead to impaired vision, changes in the cornea and decreased brain volume, all which can also affect ocular parameter measures. Barbiturates have been reported to produce effects like alcohol, and the effects of benzodiazepines and opioids seem to be more limited but still substantial.

d. Physiologic impairments, such as fatigue and changes of the intracranial pressure within the skull can adversely affect ocular parameters.

Based on the foregoing, it should be apparent that wearable face protective equipment and methods that measure ocular parameters can be valuable for assessing human health.

Definitions

The definitions that follow apply to the terminology used in describing the content and embodiments in this disclosure and the related claims.

Artificial intelligence (AI) is defined in this document and embodiments as a computer system program which attempts to implement aspects of human-level intelligence, in which a machine can learn and form judgements to improve a recognition rate for information as it is used. AI can behave in ways that both mimic and go beyond human capabilities. AI-enabled programs can analyze and contextualize data to provide information or automatically trigger actions without human interference. Artificial intelligence technologies include a machine learning (or more advanced deep learning) technology that uses an algorithm that classifies/learns the characteristics of input data by itself and an elemental technology that simulates functions such as recognition or judgment, like the human brain. The elemental technology can include a visual comprehension technique for recognizing objects as in human vision. In this document and embodiments, artificial intelligence is used with multiple indicators provided by the history, physical exam, laboratory studies and multiple methods of measuring the ocular parameters, to assess the human health condition and determine whether the data is to be used for determining normal health, abnormal health conditions, impairments, training, treatment, or as a system controller for other applications.

The autonomic nervous system (ANS) consists of the sympathetic and parasympathetic branches, both of which play roles in controlling aspects of eye function. The sympathetic branch is responsible for the "fight or flight" response. This branch controls the dilation of the pupils (mydriasis) through the action of the dilator pupillae muscle. This dilation allows more light to enter the eyes and is associated with arousal and responses to low light conditions. The parasympathetic branch is responsible for the "rest and digest" response. It is responsible for the control of constriction of the pupils (miosis) through the action of the sphincter pupillae muscle. Pupil constriction occurs in response to bright light or when focusing on nearby objects. The ANS with the oculomotor system, have distinct roles in regulating different aspects of controlling eye function. Assessment of pupil size changes associated with the ANS is valuable, as this can determine neurologic impairments, including TBI, behavioral health impairments, which occurs with substance use, and physiologic impairments, such as fatigue.

Behavioral health conditions are emotions and behaviors that impact overall physical health, such as lifestyle choices, habits, and adherence to medical treatments. This condition focuses on the actions an individual takes. In this document and embodiments this condition largely refers to substance use behaviors, where substance use entails the consumption of psychoactive substances, such as drugs or alcohol, for various purposes, including recreational, medicinal, or self-medicating reasons. The term encompasses the ingestion, inhalation, or injection of substances that can alter behavior, post-traumatic stress disorder, moods and emotions.

Biochemical health impairment in this document and embodiments refers to impairment or dysfunction in the biochemical processes within the body that can impact overall health. Biochemical processes involve the production, regulation, structure, levels, or physical properties of the biological or chemical nature of hormones, immunoglobulins, electrolytes, gases, or metabolites. This would include proteins, carbohydrates, lipids, nucleic acids, the mechanisms of enzyme action, the chemical regulation of metabolism, the chemistry of nutrition, the molecular basis of genetics (inheritance), the chemistry of vitamins, energy utilization in the cell, and the chemistry of the immune response. Most biochemical diseases affect the brain, and many lead to mental health impairments, developmental delays, behavioral problems, or neurologic handicaps.

Cognition is defined as the mental action or process of acquiring, understanding, and using knowledge through thought, experience, and the senses. In this document it represents a component of the mental processes. It encompasses various aspects of high-level intellectual functions and activities such as attention, memory, knowledge, decision-making, planning, reasoning, judgment, perception, comprehension, language, and visuospatial function.

Cognitive impairments are defined as any impairment, disease, or condition that significantly impairs cognition, as defined above, and cognitive function of the person to the point where normal functioning in society is impossible without treatment. Cognitive impairments include various disorders and impairments affecting cognitive functions including neurocognitive impairments, which are specific subset types of cognitive impairments which involves impairments in cognitive functions associated with brain structure and/or function. These impairments are commonly detected by ocular parameter measurements. Eye position and eye movement measurements can be used to assess cognitive impairments and provide key treatment approaches. Visual and cognitive processing occurs during eye fixations which makes vision-based testing, such as with ocular parameter measurements, vital as a sensitive approach in the initial evaluation of mental health conditions.

A concussion is a traumatic brain injury that results in temporary loss of normal brain function. It is characterized by immediate and transient alteration in brain function, including alteration of mental health condition or level of consciousness, that results from mechanical force or trauma. Concussions can be caused by direct trauma to the head, such as from falling, getting hit or being in an accident. They can also occur because of rapid acceleration-deceleration of the head, such as in whiplash injuries or blast injuries, such as in a war zone. A concussion can affect memory, judgment, reflexes, speech, balance, and muscle coordination and is associated with abnormal ocular parameter measures. In this document, it is used interchangeably with traumatic brain injury (TBI).

Controllers in this document and embodiments refers to electronic components or electronic devices which can regulate, manage, control, or direct the operation of other components or systems. They include, but are not limited to vehicle controllers, engine controllers, power controllers, aircraft engine controllers, vehicle control system controllers, flight controllers, remote controllers (transmitters), drone controllers, guidance system controllers, onboard system controllers, command system controllers, launch controllers, memory controller, cloud controller, and wireless local area network (LAN) controller.

The cornea is the circular transparent layer that covers the pupil, iris and anterior chamber of the eye and is the anterior one-sixth of the fibrous layer of the eyeball.

"\* MERGEFORMAT \* MERGEFORMAT Corneal components can be used for eye tracking, as beams of light striking the cornea create a reflection (e.g., a glint). Numerous corneal reflections (glints) can offer high resolution imaging of the pupil and cornea.

Dynamic eye fixation is defined as the ability to fixate on a visual target of interest, which is in motion. Dynamic eye fixation involves a series of quick, involuntary eye movements called saccades, which are responsible for shifting the point of eye fixation from one location to another. Static eye fixation refers to the ability to fixate on a stationary visual target of interest. In normal human activities, when viewing objects in the visual field, the head has natural motion or has movement and we follow moving objects or observe stationary visual targets of interest, while we are in motion. When observing a visual object of interest, it is important to have a focused position of the eye on the visual object when these objects are stationary or in motion, and the head is in motion. Our ability to maintain dynamic and static eye fixation on these visual targets while we are in motion, performing our daily activities, can provide a measure of human performance.

Emotion refers to a complex, subjective experience that involves physiological arousal, expressive behaviors, and conscious awareness. Aspects of emotion include a conscious mental reaction or state of feeling, such as sadness or joy, often accompanied by physiological changes in the body and behavioral expressions. It has a personal significance or meaningful attachment which triggers the emotional response. Emotions can influence perception, memory, behavior, and well-being. Emotion involves the integrated experience of subjective feelings, physiological arousal, and behavioral expression in response to personally meaningful stimuli.

Extended reality (XR) is an umbrella term that encompasses all immersive technologies that merge the physical and virtual worlds. Extended reality devices in this document and embodiments, refers to the spectrum or entire virtuality continuum of devices that use immersive technology to connect real environments, virtual environments, and human-machine interactions. The term extended reality (XR) includes virtual reality, augmented reality, and mixed reality. Virtual reality (VR) is defined as a fully immersive digital environmental experience which replaces the real world. It is often implemented using stereoscopic goggles. Augmented reality (AR) overlays computer-generated information on physical elements of the real-world environment. It can be implemented using smart glasses, smart contact lenses, heads up display, and helmet mounted display systems. Mixed reality (MR), an additional subset of XR, intersects and combines both AR and VR elements where the digital and real-world physical objects or elements interact in real-time providing a blended reality environment experience. It provides a higher degree of interaction and manipulation with both virtual and physical/real world objects. One example is a full immersion in a digital environment with the viewer using stereoscopic googles that combine real time video information from a scene that a user would be seeing with computer-generated information and the viewer can see, hear and touch the digital elements.

Eye components in this document and embodiments are defined as the anatomic features or distinguishing components of the eye, including the sclera, cornea, limbus, iris, pupil, eyelid and retina. Each of these components can be imaged by an eye sensor and used to measure ocular parameters and each of the components can be used to determine the position, movement, orientation, and functional activity of the eye to assess the human health condition, such as performance for individuals with normal human health, neurologic conditions, physiologic and/or biochemical impairments.

An eye imaging module in this document and embodiments refers to a device that images features and/or components of the eye and eyelids to measures ocular parameters. These measurements can include eye movement, eye position, eyeblinks and pupil size. The eye imaging module can include any mechanical, digital, or electronic apparatus for recording, storing, or transmitting visual images. Examples include still cameras, video-based cameras, event cameras which have independent pixels that respond asynchronously to relative changes in brightness generating "events" when the change exceeds a threshold, and scanners. The eye imaging module can comprise light sources (e.g., infrared light), lenses, prisms, mirrors, and other means for converting images or light paths, and detectors of the light. The means for converting the image or light path can be passive or could be active, an example would be a micro-opto-electromechanical (MOEM) system. The detector could be a photodetector (e.g., an opto-electric transducers) that convert optical signals into electrical signals. It could also be an array of electro-optical sensors, such as the charge conducting device (CCD) arrays found in some video cameras. Other types of imaging devices include CMOS imagers, single photon avalanche diode (SPAD) sensors, global shutter image sensors, single photon sensitivity sensors, high frame rate image sensors, high dynamic range vision sensors, low voltage and low power imagers, and imaging systems on a chip. This eye imaging device can integrate the sensors, processor, electronic circuitry, and external interfaces. In this document and embodiments, eye tracking, eye sensor, eye imaging module, and/or eye orientation sensor all represent an eye imaging device, and the terms may be used interchangeably to represent measurements of eye movement, eye gaze position at any given time, and measures of any of the eye features as described herein.

Eye tracking is defined as the process of measuring where we look, also known as point of gaze or gaze point. In one embodiment, a light source, such as near-infrared light, is directed towards the center of the eyes (pupil), causing detectable reflections in the pupil and cornea. The resulting reflections, the vector between the cornea and the pupil, can be tracked by an infrared camera. This is the optical tracking of corneal reflections, known as pupil center corneal reflection. The pupil provides information of gaze direction and glints inform eyeball location. These measurements can be carried out by an eye sensor or sensing device, such as an imaging device comprised of an opto-electric transducer that detects the position and movements of the eye and converts the light signal to an electric signal.

Eyeblinks are the action of closing and re-opening the eyes (e.g., eyelid movement). Eyeblinks are either voluntary, involuntary (such as a spasm), or reflex blinks (evoked by an external stimulus). A voluntary eyeblink involves cortical control. Blink patterns can be comprised of incomplete or partial blinks, prolonged eyelid closure time and short blink intervals. When the eyes are closed during a blink, there is no incoming visual information to process. Eyeblinks can indicate changes in attention, fatigue, and cognition. Specifically, eyeblink characteristics in this document include the frequency of eyeblinks or eyeblink rate, the amplitude, velocity of blinks, blink latency, and the duration of blinks which can be measured to detect different human health disorders or impairments. Eyeblink in this document is used as an ocular parameter measurement to assess eyelid performance and/or function and detect normal human health and human health abnormalities, such as a neurologic impairment, mental health condition, behavioral health condition, biochemical impairment, and/or physiologic impairment such as fatigue.

Eye fixations are periods during which the eyes remain relatively still and focused on a specific location in the visual field for a certain duration. Fixations occur when the eyes gather detailed visual information from a particular point in the visual field. During eye fixation, the eyes maintain a relatively constant gaze point. More specifically, it refers to a collection of relatively stable gaze points that are near in both spatial and temporal proximity.

Eye fixation points refer to the specific locations or areas in the visual field where the eyes come to a rest during fixations. Eye fixation points can be points or targets of interest, objects, or features in the visual scene that attract the viewer's attention. It is the stationary eye position between eye movements or saccades when observing a point target. Eye fixation points are crucial for clear vision and detailed visual processing because the eyes need to remain relatively still to gather detailed information from a specific area. During fixation, the eyes hold steady on an object, and thus eye fixation reflects attention to a stimulus and strongly correlate with task performance. Eye fixation is a static concept with most fixations lasting between 50-600 ms, but the amount of time spent on a specific fixation is dependent on both the task and stimulus. Because task performance is also correlated with effort expenditure, there is a link between eye fixation frequency and cognitive effort. Eye fixations are those times when our eyes essentially stop scanning about the scene, holding the central foveal vision in place so that the visual system can take in detailed information about what is being looked at. Eye fixation measurement includes the number of fixations, position measures, and duration of the fixation. Eye fixations are excellent measures of visual attention and visual fixation ability on an object of interest, while the head is stationary or in motion and in this document can be an accurate and predictable measure of human performance, performance for individuals with the human health condition.

Eyelid movement is defined as the motion of the eyelid (e.g., also called an eyeblink) to position the eyelid in a particular place. More specifically, it is related to the velocity of an eyeblink, the duration of the eyeblink, the amplitude, as well as the frequency of eyeblinks, and whether the eyeblink is voluntary, involuntary, or reflexive during the upward or downward motion to position the eyelid in a specific location.

Eyelid position is defined by its location and as being normal when in primary gaze (e.g., binocular fixation while looking straight ahead). For example, in the resting position the eyelid position may be open, partially open or closed.

Eyelids are thin folds of skin that cover and protect an eye. The eyelid is made up of several layers; skin, orbicularis oculi muscle (main protractor muscle which closes the eyelid), tarsal plate, levator muscle apparatus (which lifts the eyelid, exposing the cornea), and palpebral conjunctiva. The orbicularis oculi muscle helps with both voluntary closure (sleep) and involuntary closure (blink). The names "palpebral" (and "blepharal") also refer to the eyelids. The key function of the eyelid is to regularly spread the tears and other secretions on the eye surface to keep it moist, since the cornea must be continuously moist. In this document and embodiments eyelid characteristics (which include eyeblinks) can be used to assess the human health condition, such as physiologic and/or biochemical impairments and/or neurologic impairments.

Eye tracker latency is defined as the time between the eye image exposure and when the data sample is available in the application on the host computer. It includes image exposure time, image read-out and transfer time, processing time, and time to transfer the data sample to a host computer. In real-time applications, eye tracker latency is important because the interaction between the user and the application depends on how fast the gaze data is delivered Focused position of the eyes is defined as the position or orientation of the eyes to provide a clear image of a visual element, visual object, or target of interest on the fovea. In this document and embodiments, it is also referred to as eye fixation, gaze point or point of gaze during an eye fixation, to provide the highest quality of visual acuity. It is used as an important ocular parameter measure to assess the human health condition.

Forward-facing camera in this document and embodiments is a device that turns images into electronic signals. It can also be referred to as a scene camera, a front-view camera, a webcam, a surveillance camera, a collision-avoidance camera, a world-view camera, a dash-cam, or a body-cam. A forward-facing is oriented to record what is in front of a device or person, toward the surroundings. The forward-facing camera data could be integrated with eye imaging sensor data, which analyze the user's eye movements, to determine the direction of gaze.

Foveated rendering refers to the technique of enhancing the subject's point of focus or gaze point, by providing the highest-definition regions on that of the fovea of the eye and reducing the resolution in the peripheral vision. While using the technology described herein, the area of the display where the user is looking is rendered with high detail and resolution, while the peripheral areas are rendered with lower detail or resolution. Foveated rendering can significantly improve performance in VR, AR, MR, or XR, and other smart eyewear applications described herein, allowing for smoother frame rates and more immersive experiences without sacrificing visual quality in the user's primary field of view.

Functional activity of the eye is defined broadly as the ocular parameters and other eye activity described herein, which provides visual function to maintain good visual acuity. Measurements of functional activity include the ocular reflexes, eye gaze position or gaze point, eye fixation, eye orientation, eye position, and movements of the eye including pupil size changes. This functional activity also includes eyelid movement (e.g., an eyeblink), which provides protection to the eye. Fundamentally, movements include, saccades, (which abruptly change the point of eye fixation), head static smooth pursuit, vestibular ocular reflex, vestibular ocular reflex suppression, vergence, (which align the fovea of each eye with targets located at different distances from the observer), pupil size/movement changes, (which controls the amount of light which reaches the retina and maximizes visual acuity), and eyeblinks, (which protects and lubricates the eye). All of these functional activities ultimately are designed to maintain maximal visual acuity with daily activities. Measures of functional activity in this document and embodiments assess eye fixation ability, performance for individuals with normal human health, and can detect an abnormal health condition, such as neurologic conditions, mental health conditions, behavioral health conditions, biochemical impairments, physiologic impairments including cognitive impairments, fatigue as well as provide health-related biomarkers for early treatment, monitoring, visual training or rehabilitation for these abnormal conditions.

Gaze refers to the direction in which a person is looking. It is the ongoing orientation of the eyes in relation to the environment or a specific object being viewed. Gaze can be dynamic, involving shifts in direction as a person explores their surroundings or focuses on different objects. Gaze can also be considered as a vector that indicates the line of sight from the eyes to a particular location. It encompasses various movements and involve a sequence of eye fixations on different objects as an individual visually explores their surroundings.

Gaze point refers to the instantaneous spatial location of the visual axis landing on the visual stimulus or visual target of interest. It refers to the specific location in a person's visual field where their eyes are directed at a particular moment. It is a snapshot of where the eyes are looking in terms of both an x and y coordinate and a timestamp corresponding to its measurement. Gaze points can change rapidly as a person looks around, scans a scene, or follows moving objects. The gaze point provides information about the current focus of attention. If a series of gaze points is very close, in time and/or space, this gaze cluster constitutes an eye fixation, denoting a period where the eyes are locked towards an object. Gaze can serve as a reliable indicator of attention and cognitive effort. In this document and embodiments, gaze and gaze point are important ocular parameter measurements in this human health system described herein for determining the human health condition.

Head static smooth pursuit is defined as the voluntary movement of the eyes in response to tracking a moving visual object, while the head is motionless. Such movements are under voluntary control in the sense that the observer can choose whether to track a moving stimulus. These movements are described to be smooth, continuous, conjugate eye movements with velocity and trajectory, determined by the moving visual target. However, the eyes are in continual small-scale motion, showing irregular drift and tremor, interspersed by miniature saccadic movements (less than 0.5 degrees). With the naked eye, head static smooth pursuit movement appears smooth, but with high-speed eye imaging devices, the movements are not entirely smooth at all, but can have an altered appearance due to the presence of saccades (covert or overt) or saccadic intrusions which can be associated with underlying neurologic conditions, or other physiologic or biochemical impairments. There are separate mechanisms of control for horizontal and vertical head static smooth pursuit tracking. Head static smooth pursuit eye movement can be divided into two stages: open-loop pursuit and closed-loop pursuit. Open-loop pursuit is the visual system's first response to a moving object and typically lasts approximately 100 msec. Therefore, this stage is ballistic and visual signals have not yet had time to correct the ongoing pursuit velocity or direction. The second stage of pursuit, closed-loop pursuit, lasts until the pursuit movement has ceased. This stage is characterized by the online correction of pursuit velocity to compensate for retinal slip. In the closed-loop phase, the eye angular velocity and target angular velocity are nearly equal. Pursuit eye movements are initiated within 90-150 msec, while typical latencies for voluntary saccades are in the order of 200-250 msec. Head static smooth pursuit is an important ocular parameter measurement for assessing neurologic conditions, mental health conditions, behavioral health conditions, biochemical impairments, and/or physiologic impairments. Measurements of head static smooth pursuit ocular parameter include acceleration, accuracy, latency, and velocity.

Head static smooth pursuit acceleration refers to the rate of change of the eye velocity. The first approximately 20 milliseconds of pursuit tend to be the same regardless of target parameters. However, for the next 80 milliseconds or so, target speed and position have a large effect on acceleration.

Head static smooth pursuit accuracy is defined by the ability of the eyes to closely follow a moving object. The pursuit of visual targets moving with velocities of greater than 30°/s tends to require catch-up saccades. Head static smooth pursuit accuracy represents how closely the percentage of time the smooth pursuit velocity value remains within the target velocity value.

Head static smooth pursuit latency is defined by the time from target appearance to the beginning of pursuit. It is measured from traces of eye velocity. It is often calculated by finding the intersection between two regression functions, one fitted to velocity about the time of target appearance, and the second fitted over the initial part of the pursuit response.

Head static smooth pursuit velocity refers to the speed of the eye movement (velocity) which usually rises to a peak, following pursuit initiation, and then either declines slightly or oscillates around the target velocity. This peak velocity can be used to derive a value for gain (peak velocity/target velocity). It is usually near the velocity of the target. Instead of using peak velocity, measures of velocity at times relative to either target appearance or pursuit initiation can be made.

Health-related biomarkers are broadly defined in this document and embodiments as an objective, accurately measurable and reproducible ocular parameter indicator of an individual's medical signs or conditions. They are components, products, or processes of the body that can be objectively measured and evaluated as an indicator of biological or physiologic processes. In this document and embodiments, biomarkers represent the signs and features of neurologic conditions, mental health condition, behavioral health conditions, biochemical impairments, and/or physiologic impairments that can be detected by measured ocular parameters. These biomarkers can serve as early warning systems for health and may be a single characteristic or a panel of multiple characteristics. A biomarker can represent a measured ocular parameter indicator of pharmacologic, physiologic, or biochemical responses to a therapeutic intervention, including training, visual rehabilitation and/or pharmacological therapeutics.

Human health condition is a multidimensional concept, requiring multiple indicators and multiple methodologies for adequate measurement. It represents an individual's level of wellness and illness, mentally and physically, and in this document and embodiments takes into account the measures to assess the presence of neurologic, biochemical and/or physiological health and function, mental and behavioral health, as well as performance for individuals with normal human health. It can be based on the individual's medical history, physical examination, assessment of laboratory studies, medications, existing disorders, impairments, or disabilities.

Internal body medical imaging is the technique or process of imaging the interior of a living organism for clinical analysis and/or medical intervention. Examples include 2-dimensional radiography, x-ray computed tomography (CT), magnetic resonance imaging (MRI), nuclear medicine such as PET scanners, medical ultrasound imaging, elastography, photoacoustic imaging, echocardiography, functional near-infrared spectroscopy, and magnetic particle imaging.

The iris is the colored ring portion of the eye. It is comprised of muscles microvessels, pigment cells and connective tissue. The color of the iris and other components are unique to each individual. The muscles of the iris control the pupil diameter and the amount of light entering the eye and the pigment of the iris serves to block out light, allowing it to only enter through the pupil opening. The iris muscle folds like an accordion when the pupil expands. Because of this accordion-like movement when the pupil constricts, the pleated folds can easily be visualized and in the pleats, the micro-blood vessels that nourish the iris are seen as very small white lines. The iris components can be imaged by an eye sensor and used to measure ocular parameters to determine the position, movement, orientation, and functional activity of the eye to assess the human health condition, such as performance for individuals with normal human health, neurologic impairments, physiologic and/or biochemical impairments. Because of the uniqueness of the iris with each individual, scanning iris components can act as a controller to open and operate an electronic device or wearable device and establish or determine which ocular parameter testing or training programs are needed, based on the private information stored in a personal health database.

The limbus is the junction of the white opaque sclera and transparent cornea (e.g., corneal border) and is approximately 1.5 mm wide. The limbus can be imaged by an eye sensor and used to measure ocular parameters to determine the position, movement, orientation, and functional activity of the eye to assess the human health condition.

Machine Learning is defined as the science of getting computers to learn and act like humans, and improve their learning over time in autonomous fashion, by feeding them data and information in the form of observations and real-world interactions. Machine learning fundamentally is the technologies and algorithms to parse data, automatically learn insights and recognize patterns from data, and applying that learning to make increasingly better decisions. This entails getting computers to act without being explicitly programmed and is based on algorithms that can learn from data without relying on rules-based programming. Deep learning, an advanced method of machine learning, goes a step further. Deep learning models use large neural networks. These are networks that function like a human brain to logically analyze data, to learn complex patterns and make predictions independent of human input. Examples of machine learning in embodiments herein can include, but not limited to artificial neural networks, association rule learning, Bayesian networks, classifier learning, decision tree learning, deep learning, inductive logic programming, regression models, reinforcement learning, representation learning, rule-based machine learning, similarity and metric learning, and sparse dictionary learning.

Mental Health refers to an individual's emotional, psychological, and social well-being. Mental health conditions refer to mental illnesses or impairments which affect a person's thoughts, emotions, behavior, or a combination of these aspects. These conditions can significantly impact an individual's daily functioning, relationships, and overall well-being. Mental health conditions are diverse and can range from relatively common conditions, such as anxiety, attention-deficit/hyperactivity disorder (ADHD), and in this document and embodiments includes those conditions of cognitive impairments.

Metabolic dysfunction refers any abnormality, disturbance, or impairment in the normal operation of metabolic processes. These processes are comprised of chemical reactions that occur within humans to maintain life. These processes are essential for the growth, development, energy production, and maintenance of the structure and function of cells. It includes those abnormalities, disturbances, or impairments which negatively alters the body's processing and distribution of enzymes, hormones, macronutrients such as proteins, fats, carbohydrates or impaired organelle function involving human organ systems. An example of metabolic dysfunction is a hormone abnormality like that of diabetes mellitus.

Mood refers to a person's emotional state or the prevailing atmosphere or feeling of a particular situation or environment. Specifically, it is a pervasive and sustained feeling tone that is experienced internally and impacts a person's behavior and interactions. Moods are typically described as having either a positive or negative valence and is distinct from emotions or feelings, which are more specific, intense, and provoked by particular stimuli or events.

A neurocognitive impairment is a neurologic condition defined as an impairment in the cognitive function due to an underlying neurologic or medical disease or impairment affecting the structure or function of the brain. It includes those cognitive impairments due to Alzheimer's Disease, Parkinson's Disease, Huntington's Disease, Lewy Body Dementia, frontotemporal impairments and neuroviral associated impairments. It represents underlying brain pathology that results in a loss in cognitive abilities such as memory, problem solving, executive function, intellect, and perception. In this document and embodiments, it represents a subset under the broader category of cognitive impairments but seen with brain disease or impairments of the central nervous system.

A neurologic condition is defined in this document and embodiments as an impairment or condition that affects the brain, the spinal cord and/or nerves found throughout the human body, resulting in physical dysfunction. Structural, biochemical, physiologic, or electrical abnormalities in the brain, spinal cord or other nerves can result in a large range of symptoms.

Ocular Parameters are measurable factors that determine the components, actions, processes, behavior and functional ability of the eye, eyeball, and eyelid. Included in ocular parameters are eye position, eye and eyelid movement responses which can be detected or measured, including saccades, vergence, head static smooth pursuit, pupil size, eyeblinks, vestibular ocular reflex, vestibular ocular reflex suppression, and the focused eye position (e.g., eye fixation or gaze point). Reflexes included in the measured ocular parameters or eye movement responses include the pupillary light reflex, pupillary dark reflex, near accommodative triad, corneal reflex, blink reflex, and vestibular ocular reflex. The purpose of having eye movements is to maintain constant foveation of an object of interest or to foveate a target quickly. Measuring movements of eye includes the extraocular muscles (which move/rotate the eye), the ciliary muscles (which helps to focus by changing the lens shape), the levator (which raises the eyelid), and the pupillary muscle (which dilates or constricts the pupil).

Ocular reflexes are involuntary responses that are usually associated with protective or regulatory functions They require a receptor, afferent neuron, efferent neuron, and effector to achieve a desired effect. Examples of an ocular reflex include pupillary reflex, and vestibular ocular reflex.

Oculomotor system is defined as the part of the central nervous system (CNS) centers, complex CNS connections or pathways, numerous peripheral inputs, cranial nerves III, IV and VI and the extraocular muscles, which functions mainly in maintaining visual stability, aligning, and controlling eye movements. It is made up of many brain areas that cooperate to stabilize images of interest on the high-acuity part of the retina. Assessment of impairments in oculomotor function is useful to detect visuomotor impairments due to a closed head injury and other neurologic and mental health conditions, as well as biochemical and physiologic impairments.

An opto-electric transducer is defined as a device that converts an optical signal into an electrical signal. Examples of such a device include photodetectors, photosensors, charge conducting devices (CCDs), complementary metal-oxide semi-conductor devices (CMOS), micro-opto-electro-mechanical-systems (MOEMS), microelectromechanical system (MEMS), and photodiodes.

Performance enhancement in this document and embodiments is defined as activities to improve human capability to do a task and/or improve health. Performance enhancement can comprise visual rehabilitation and/or visual training. Performance enhancement can be applied to ocular parameters discussed herein, to achieve a normal human health condition or supranormal ability.

A photodetector is defined as a device that turns light into an electrical signal. This can be an opto-electric transducer which converts the optical signal into an electrical signal. Multi-element photodetectors can be used for imaging. Photodetectors could work with visible light, they could work with invisible light (such as infrared or ultraviolet), or they could work with a combination of visible and invisible light. A non-imaging photodetector is a device that turns light into an electrical signal but has too few elements to produce an image. Thus, a non-imaging photodetector might comprise only one light-sensing element that turns received light into a magnitude based on the intensity of the light received. A non-imaging photodetector might comprise two light-sensing elements that allow the detection of an edge, but not an image, and therefore can be called an edge-detection photodetector. A non-imaging photodetector might also comprise a two-dimensional pattern of three or four photodetectors, that allow the detection of an edge in more than one dimension, but not an image.

Physiologic health impairment is defined as impairment of the normal biological functions of organs, tissues, or cells of humans. It also includes impairments affecting the vital physiologic functions, growth and development, the absorption and processing of nutrients, the synthesis and distribution of proteins and other organic molecules, and the functioning of different tissues, organs, and other anatomic structures, such as the pulmonary, cardiac, and neurologic systems. Examples of physiologic health impairments includes, but not limited to, fatigue, diabetes mellitus, abnormal intracranial pressure impairments, kidney disease, autoimmune impairments, motion sickness, dizziness, eye movement impairments, retinopathy, and visual impairments.

The pupil is the black opening located in the center of the iris of the eye that allows light to strike the retina. In optical terms, the anatomical pupil is the eye's aperture, or the size of the circular opening through which light passes. Pupil size is a typical characteristic of the pupil that can be measured. In this document and embodiments, pupil size can also be the same as pupil diameter. The diameter of the pupil can be modulated by light, cognition, sleep, drugs and arousal. Dilation of the pupil is known as mydriasis and contraction as miosis. The size of the pupil, measured as diameter, can be a symptom of an underlying disease. Pupil center corneal reflection (PCCR) can be used as a method for eye tracking, in which the pupil and corneal reflections are measured. Using such measurements, the eye position, point of gaze, orientation, and eye movements can be determined with advanced mathematical analysis.

Pupil performance refers to the response of the pupil to a given stimulus, activity and/or human health condition. Pupil performance can be determined by measurements such as changes in pupil size, changes in pupil dilation, pupil response latency, and pupil response duration. Pupil performance measurement can be used to diagnose a neurologic condition and pupil size changes provide clinical health-related biomarkers.

Pupillary light reflex refers to an autonomic reflex that constricts the pupil in response to light, thereby adjusting the amount of light that reaches the retina. Pupillary constriction occurs via innervation of the iris sphincter muscle, which is controlled by the parasympathetic system.

Pupil size changes is defined in this document and embodiments, as the measures of minute fluctuations in pupil diameter, (e.g., pupil size) in response to a stimulus. This includes pupil movement features as a function of time, to assess pupil performance. Pupil measures includes movement features of pupil diameter, dilation information including acceleration, latency, duration of changes in size, amplitude changes, and constriction information also including latency, duration as well as amplitude changes. It also includes peak and average constriction velocity from the iris sphincter muscle as well as dilation velocities of the dilator pupillae muscle under numerous stimulus conditions, including dim pulse, dim step, bright pulse, bright step, bright red step, and bright blue step. Pupil performance or pupil size changes, which results from measures of pupil size and other pupil features described in this document and embodiments, can be an important health-related biomarker.

Rehabilitation is defined as restoration, especially by therapeutic means, to an improved condition of neurologic, physical, physiologic behavioral, mental, and/or cognitive function. This includes the recovery, restoring, or maintaining a function with therapy. It can also include training to enhance existing abilities and achieving higher personal performance levels as well as improvement of abilities beyond normal levels. Rehabilitation and training share similarities in using structured exercise protocols and goal-oriented programs. In this document and embodiments both rehabilitation and training utilize visual methods and systems in XR devices to acquire eye data as described herein and the training and rehab protocol is responsive to the recorded eye information.

Saccades are defined as rapid, ballistic movements of the eyes that abruptly change the point of eye fixation when gazing from one object to another (i.e., rapid changes in eye orientation). The eye movements between fixations are generally referred to as saccades. Like eye fixations, saccades are made up of multiple gaze points and they have a start and end point each with a timestamp. Measures can be made at which point saccades occurred in time and their duration. The purpose of saccades is to alter the gaze from one object of interest to another under effort of will (voluntary saccades), to alter the gaze to a sudden event in the periphery (reflex saccades), to correct small errors of eye fixation (fixational microsaccades), and to correct small errors in pursuit (catch-up or back-up saccades). Vision is disrupted during saccades, a phenomenon called saccadic omission. Retinal blur occurs as the images move rapidly across the retina because the retina has limited temporal resolution. Saccade parameters of measurement includes accuracy, amplitude, inhibition, latency, duration, velocity with initial acceleration and peak velocity, frequency, and number over time. These quantitative measurements of saccades are used to assess the function of the oculomotor system, to investigate the effects of drugs or lesions, and to aid diagnosis of neurologic impairments or locating brain lesions in the central nervous system.

Saccade accuracy refers to the eye's ability to quickly move and accurately shift from one target fixation to another. Accuracy refers to how well the calculated eye fixation location matches actual eye fixation location. This is expressed in degrees of visual angle (a half circle has 180° of visual angle). Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude refers to the size of the eye movement response, usually measured in degrees or minutes of arc. The amplitude determines the saccade accuracy. This is sometimes referred to as gain. It is also described as the angular distance the eye travels during the movement.

Saccade Inhibition refers to an absence or near-absence of saccades initiated around 80-120 msec following a brief visual distracting effect that interferes with the production of scanning saccades.

Saccade latency refers to the time taken from the appearance of a visual target to the beginning of an eye movement in response to that target. Normal saccades have a latency of typically about 200 msec. Many factors influence saccade latency. Longer latencies occur with weak (dim or low contrast) targets, unpredictable targets, and with older individuals. Shorter latencies occur with brighter visual targets, predictable targets, with auditory stimuli, and with younger individuals.

Saccadometry is defined as the functional evaluation of saccadic eye movements with the neural pathways and frontal, parietal and occipital areas of brain involvement. Saccadometric measures can include accuracy, latency, duration, frequency, and velocity of a saccade or multiple saccades in combination with the position or movement of each eye. The two most common assessments are the prosaccade and anti-saccade. A prosaccade requires an eye-movement toward target jumps. Specifically, individuals are instructed to look at a center target and then need to direct their gaze toward a target dot appearing at the periphery as quickly and as accurately as possible. After viewing the peripheral target, they then return to the center target dot and wait for the next target jump. By contrast, anti-saccade tasks typically require an eye-movement of equivalent amplitude to be executed rapidly, but in the opposite direction. The technology discussed herein and in embodiments can utilize saccadometry as a health-related biomarker to enhance the diagnosis and monitoring of neurological conditions, such as traumatic brain injuries.

Saccade velocity is defined as speed measurement during the eye movement. High peak velocities and the main sequence relationship can also be used to distinguish micro-saccades from other eye movements such as ocular tremor and ocular drift. Saccades have a very high velocity, up to 800 or even 1000 degrees per second for very large saccades. Saccade velocities follow a very specific, predictable pattern such that the peak velocity of the saccade is dependent on its amplitude. Saccades are reprogrammed after each eye fixation period. In most cases, if a target moves during a saccade, the saccade in progress is not modified and the next saccade will not occur until one latency period after the end of the first saccade. Inaccurate control of saccades is termed saccade dysmetria, undershoots are referred to as hypometric and overshoots are termed hypermetric. Peaks corresponding to saccadic movements show a linear relationship between the peak velocity of a particular saccade and the amplitude. Once the peak velocity has been reached, the amplitude of the saccade, and therefore the final position of the eye after the saccade can be determined with a high degree of accuracy. Saccades have fixed relationships between the amplitude, duration, and peak velocity. There are main sequence parameters and relationships. Generally, in normal individuals there is a linear relationship between saccade amplitude and duration.

Sampling rate of eye tracking (or sampling frequency) refers to how many times per second or the frequency which eye position is measured. This can be reported in Hz, frames per second, or in "events" when using dynamic vision sensor pixels sampling. The human eye moves at speeds exceeding 300°/sec. The eye's acceleration regularly reaches values around 24,000°/sec$^2$. Common sampling rates are 1,000 Hz, 500 Hz, 250 Hz, 120 Hz, and 90 Hz. During normal adult reading, eye fixation durations typically vary from about 100-800 milliseconds, with the average being approximately 250 milliseconds. Higher sampling rates produce better temporal accuracy when measuring the duration of eye fixations and saccades. Cameras with many eye or gaze-tracking systems have fundamental bandwidth and power limitations, limiting data acquisition speed measuring frame rates. Higher gaze tracking can be achieved with near-eye gaze tracking of pupil motion using dynamic vision sensors. The dynamic vision sensor pixels instantly samples pupil movement by the incident irradiance and provides separate events of pixel location, created by assessing and processing each individual pixel in the image sequentially with time-stamped signal changes. Pixel location, time of measurement, as well as the sign of the change in contrast is noted. This results in more efficient bandwidth use than frames and improved speed and power consumption. A sensor with a high peak sampling rate can detect the eye moving more quickly and characterize that motion with higher fidelity. Each dynamic vision sensor pixel responds independently from adjacent pixels when it sees a contrast change and is referred to as an event. Sensors combining frame rates with the pixel events can provide much faster eye tracking ability. In this document and embodiments, multiple types of eye tracking sensors can provide high sampling rates of eye tracking including these types of event-based sensors, microelectromechanical system (MEMS) sensors, or other types of eye imagine modules capturing frame rates, and/or a combination of these.

The sclera is the white portion of the eyeball and its related blood vessels. Reflections from light sources on the sclera can be used for eye tracking. A glint can be identified as a reflection of light from a sclera characteristic. Glints can be used to measure eye movement, orientation and position of the eye.

Slippage is defined as when an imaging device viewing a subject's eye moves out of phase with the subject's head. With head worn XR devices, slippage occurs when the headset's position shifts on the user's face, which changes the position of the eye tracking sensors relative to the eye at the time the device was calibrated and results in a deterioration of eye tracking signal quality. The degree to which slippage may occur and the resulting impact on eye tracking signal quality may be affected by a number of factors, such as the quality of the straps used to secure the headset to the user's head, the robustness of the hardware to repositioning, and the degree to which an individual user may induce slippage through head movement. This can be mitigated by the use of the quality of the head band, a snug fitting, and lighter hardware which does not project to far outward from the head. A software algorithm for slippage offset can also account for slippage and compute an appropriate value that can be used to synchronize sensor data.

Vergence is the ability of shifting our point of gaze from a far object to a near object, causing our eyes to converge. At the same time, the lenses of our eyes modify their focus (accommodate), and our pupils often constrict. The mechanism and control of vergence eye movements involves complex neurological processes that can be compromised in individuals with traumatic brain injury, resulting in a wide range of vergence dysfunctions and related near-work symptoms, such as oculomotor-based reading problems. Overall, vergence is an important component of the oculomotor system's role in maintaining eye fixation for both near and distant objects. Convergence is the simultaneous inward movement or orientation of both eyes toward each other, usually to maintain single binocular vision when viewing an object more closely. Divergence is the simultaneous outward movement or orientation of both eyes away from each other, usually to maintain single binocular vision when viewing an object which is further away. Typically, vergence velocity responses do not exceed 60 degrees/second. Vergence orientation movements tend to have relatively long latencies, typically on the order of 150-200 msec. Measurements of vergence can be performed while visually following the target element of interest, which moves in a smooth transition to different depths (e.g., dynamic vergence) or in a sequence of steps with the head stationary or head in motion. Such measurements can also include a binocular precision index (BPI) and binocular accuracy index (BAI) to quantify changes of convergence and divergence peak velocity, amplitude, symmetry, and latency. Vergence can accurately be measured with an extended reality device with the systems and methods discussed in this document.

Vestibular Ocular reflex (VOR) refers to an eye movement in response to stimulation of the inner ear balance system. In this document and embodiments, it can be measured without direct measurement of head movement. Measures of VOR can include velocity, gain, phase, symmetry, eye movement direction and saccadic responses to the inner ear stimulation.

Vestibulo-ocular Reflex Suppression (VORS) refers to the ability of the brain to suppress vestibular signals in response to head and eye movement in the same direction as that of a moving target, while maintaining fixation on the target. The VOR is suppressed to allow the eyes to accurately track a moving target, ideally at the same velocity as the target, while the head is also moving. This suppression is a part of the brain's ability to integrate and prioritize sensory inputs from different systems, such as the visual and vestibular systems, to maintain spatial orientation and stability. Like VOR assessment above, vestibular ocular reflex suppression can be measured without direct measurement of head movement. Analyzing the recorded eye movements, particularly the compensatory eye movements (saccades) that occur to stabilize gaze during head movement, can also be used to assess the integrity of the VOR.

Figures Describing Ocular Parameter-Based Human Health Assessment

Figure 14:
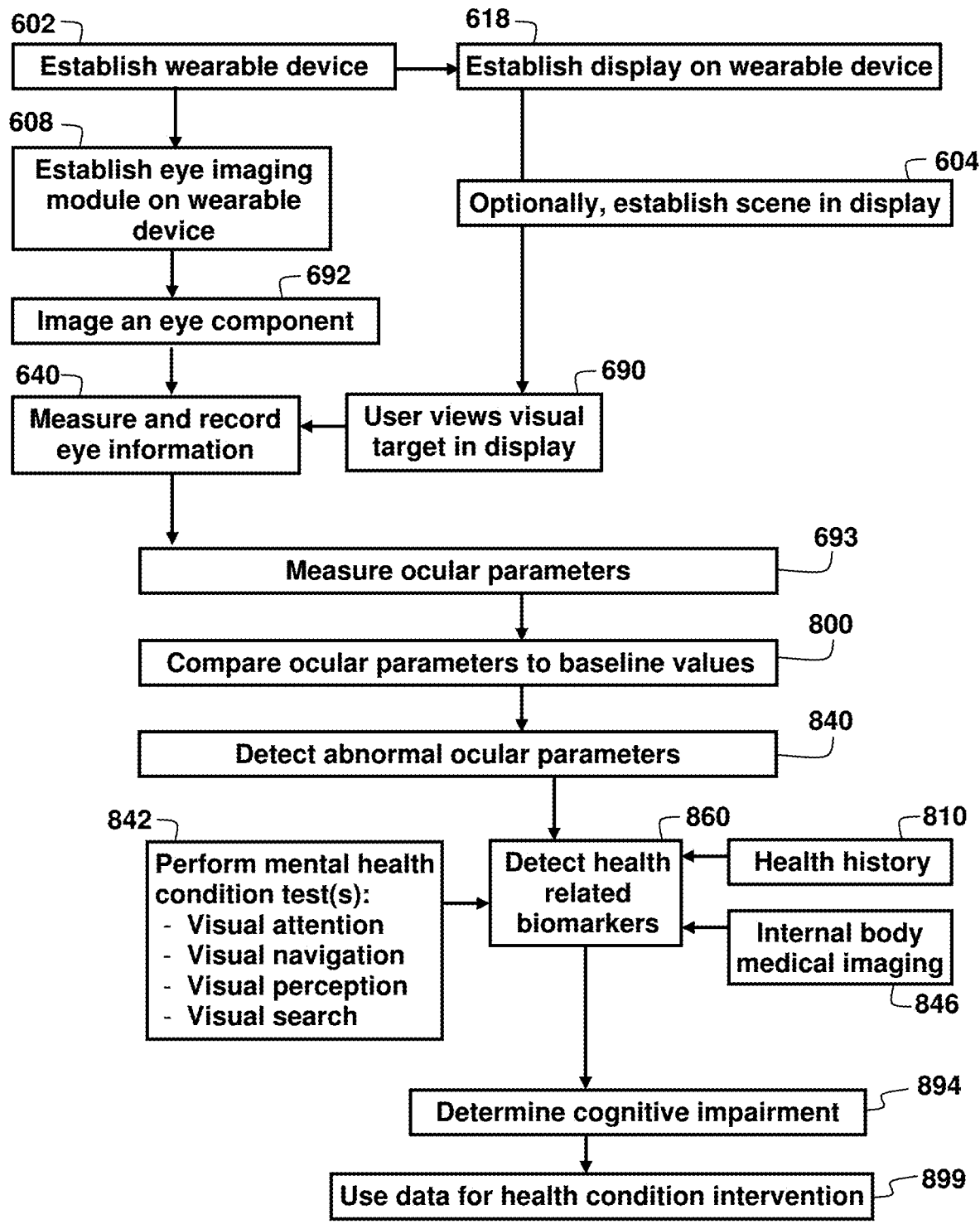
FIG. 14 shows a method for assessing mental health conditions.
Figure 15:
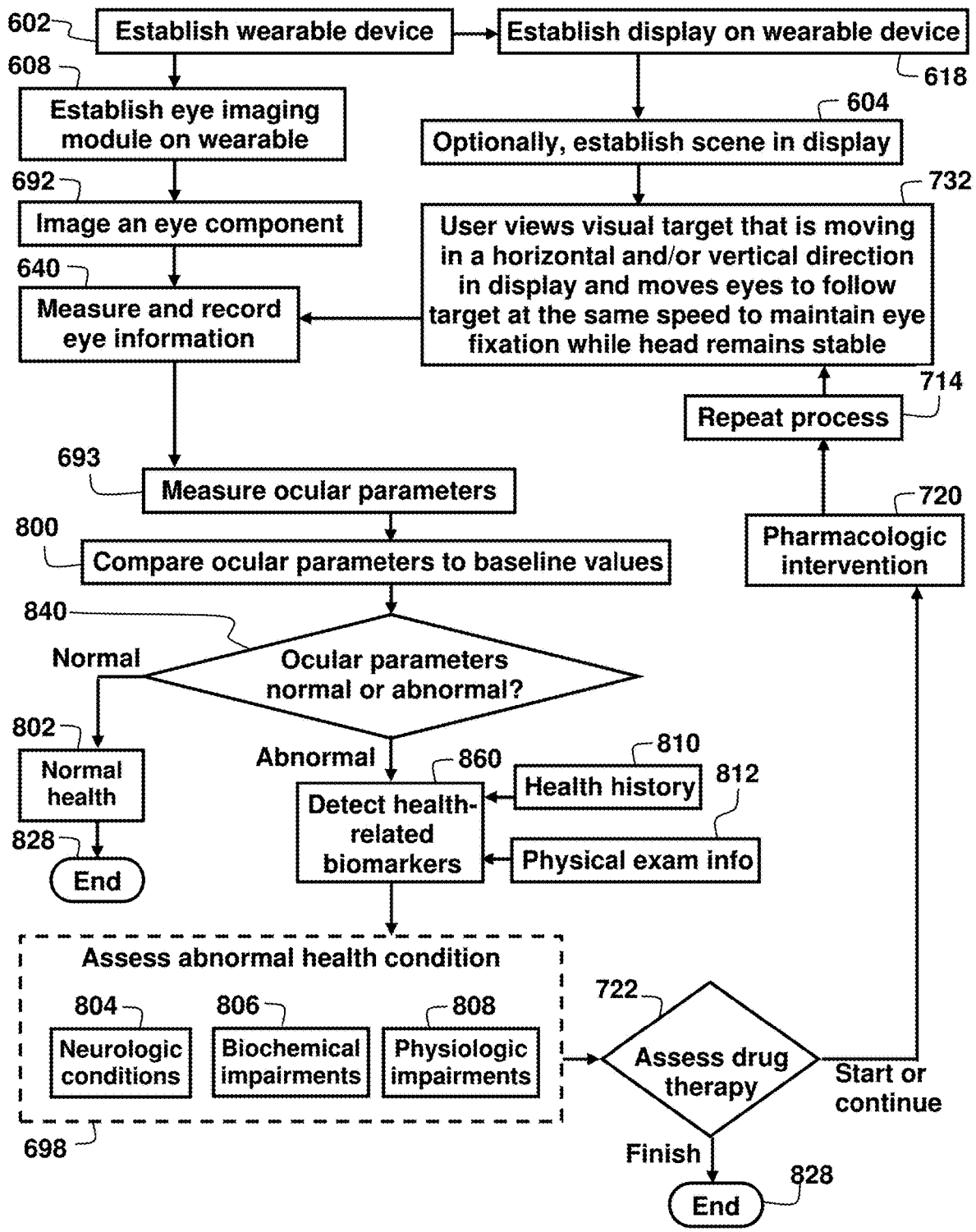
FIG. 15 shows a system for pharmacologic intervention and assessment.
Figure 16:
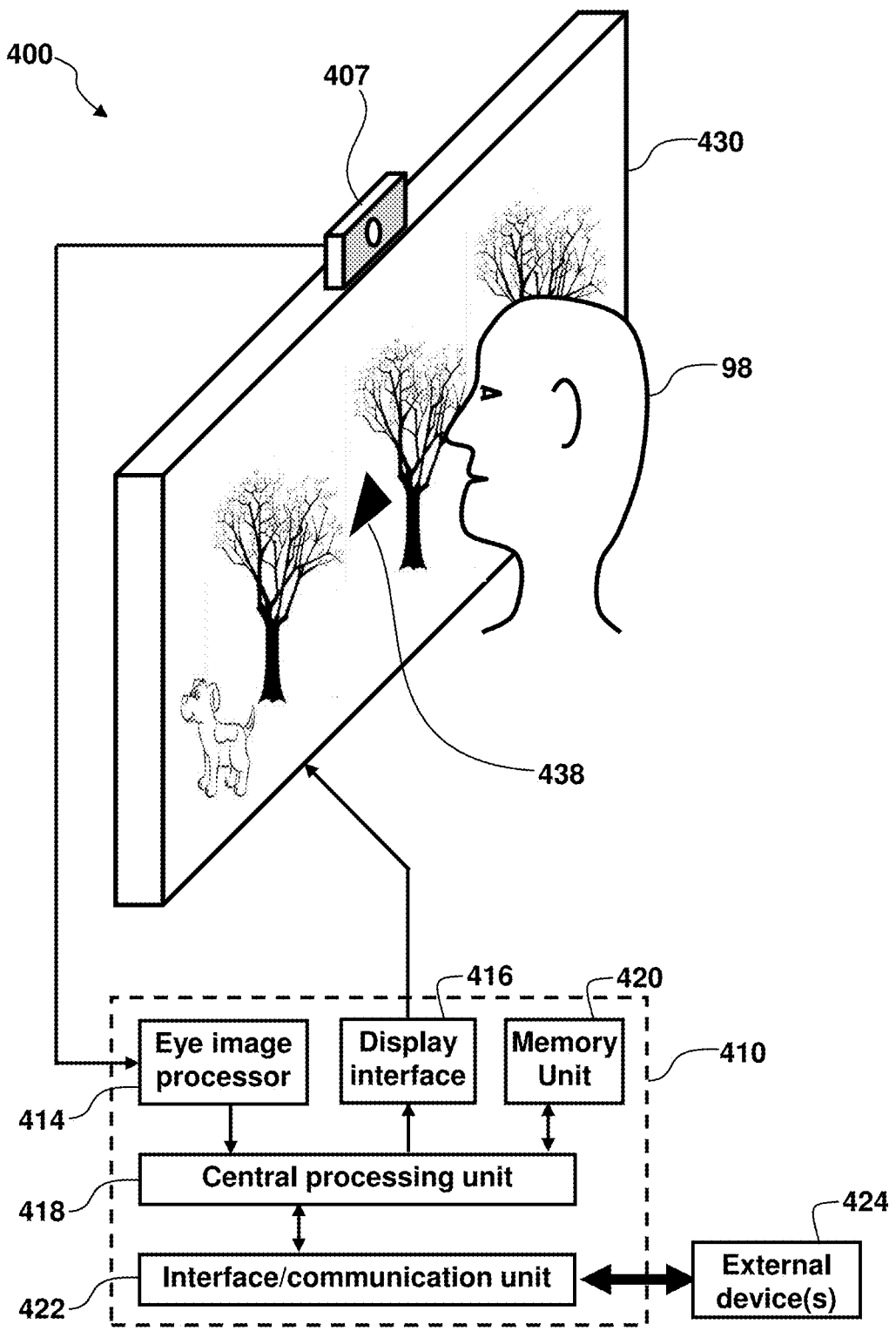
FIG. 16 is an immersive system to assess health that doesn't use wearable components.

Referring now to the figures, FIG. 1 shows a generalized method for observing eye information to measure ocular parameters with the objective of using this information for health condition intervention 899 or as input for control of a system 821. This generalized method starts by establishing a wearable device 602. Next, an eye imaging device (e.g., module) 608 is established on the wearable device 602. A display 618 is also established on the wearable device 602. The eye imaging module 608 is used to image an eye component 692, while the user is viewing the visual target on the display 692. The eye component being measured in step 692 can comprise a retina, sclera, cornea, iris, limbus, pupil, or eyelid. In the embodiment of FIG. 1 and other embodiments described and illustrated herein, an infrared light source in the eye imaging module 608 could be used to improve measurement of the eye components. The user is instructed to view a visual target in the display 690. This visual target seen in the display can be seen overlying normal physical environment elements or in an alternative embodiment, the visual target used for assessing ocular parameters can be viewed in the physical environment in a 3-D manner or as a virtual hologram in the physical environment. The displayed visual target can have numerous movement features, such as rotation. The user can interact with the virtual visual target in the physical environment. The physical environment can also have simulated features, such as motion to add to as distraction, which can be used for more intensive assessment, training, or rehabilitation. These features of the visual target viewed in FIG. 1 can also be applied to viewing and interacting in a similar manner with the visual target in FIG. 5, FIG. 6, FIG. 7, FIG. 8, FIG. 9, FIG. 10, FIG. 11, FIG. 12, FIG. 13. FIG. 14, FIG. 15, and FIG. 16. The eye imaging module 608 images the eye component 692, and eye information is measured and recorded 640, in response to the users view of the visual target in the display 690 or as seen as a virtual target or element in the physical environment (FIG. 16). The eye information that is measured and recorded in step 640 can comprise eye position information, horizontal eye movement information, vertical eye movement information, pupil size information, eyelid information (and more specifically eyeblink information), and any combination of this information or anything similar capable of being understood by anyone skilled in the art.

The eye information from step 640 can then be used to measure ocular parameters, as shown at step 693. Examples of ocular parameters that embodiments of the invention can be configured to measure can include saccades (see FIG. 6 and FIG. 12), vestibular ocular reflex suppression (also on FIG. 6), vergence (see FIG. 7), head static smooth pursuit (see FIG. 8), pupil size changes (see FIG. 9), eyeblinks (see FIG. 10), eye fixation and/or gaze (see FIG. 11), and/or vestibular ocular reflex (also on FIG. 12).

Further referring to FIG. 1, the ocular parameters measured in step 693 can be compared to baseline values (i.e., normal values), as shown at step 800, to determine if ocular parameters 840 are normal. If ocular parameters indicate normal health 802, the process ends, as shown at 828. If ocular parameters are abnormal, the ocular parameter information can be supplemented with physical exam information 812 and health history (which can comprise prior lab results, imaging, and vital signs) 810, to detect health-related biomarkers 860, which in turn can be used to assess an abnormal health condition, at step 698. This assessed abnormal human health condition 698 can be categorized into:

a) Neurologic conditions, such as traumatic brain injury (TBI), shown at 804;

b) Mental health conditions, such as cognitive impairment, shown at 803;

c) Behavioral health conditions, such as substance use, shown at 805;

d) Biochemical health impairments, such as metabolic dysfunction, shown at 806; and e) Physiologic health impairments, such as fatigue, shown at 808.

Regarding 810 (health history), diagnosis of a health condition has been described as both a process and a classification scheme, or a pre-existing set of categories agreed upon by the medical profession to designate a specific condition. The working diagnosis may be either a list of potential diagnoses (a differential diagnosis) or a single potential diagnosis. Generally, there are four types of information-gathering activities in the diagnostic process: 1) taking a clinical history and interview; 2) performing a physical exam; 3) obtaining diagnostic testing; and/or (4) sending a patient for referrals or consultations. A subject's clinical history includes documentation of the current concern, symptom history, past medical history, family history, social history, and other relevant information, such as current medications (prescription and over the counter) and dietary supplements. An accurate history facilitates a more productive and efficient physical exam and the appropriate utilization of diagnostic testing. The medical interview is the process of gathering data that will lead to an understanding of the disease and the underlying physiological process.

Biomarkers (step 860) are important. It is biomarkers that enable us to distinguish Alzheimer's from Parkinson's, etc. and treatment related to early biomarker identification can prevent symptoms and enable more rapid recovery of impairments.

Further referring to FIG. 1, the assessed human health condition from 698 can be used to train for health condition intervention, as shown at 898. This health condition intervention could be for training, treatment, and/or rehabilitation as is further described with reference to FIG. 13. A specific rehabilitative program could be used for treatment of the abnormality identified with the human health condition. Embodiments can enable individuals to reach a higher level of performance in their occupation, enable them to have increased ocular performance functions when participating in their usual occupational or play activities as well as enabling cognitive training and rehabilitation. Health condition intervention 899 could be related to mental health, as will be further described with reference to FIG. 14. Health condition intervention 899 could comprise a drug therapy 720, as will be further described with reference to FIG. 15.

FIG. 1 also shows that data from the generalized method for assessing human health condition could be used as input for controlling a system, as illustrated at step 821. One example of system control in step 821 might be the use of health condition information from step 698 to control a vehicle, and more specifically to determine whether the human, who has been assessed at 698, is capable of safely operating the vehicle.

When assessing mental health conditions numerous visual assessments can be performed while viewing visual targets. For example, ocular parameter measurements, including head static smooth pursuit, vestibular ocular reflex (VOR), vestibular ocular reflex suppression (VORS), pupil size changes and eyeblink information use visual targets for assessment, and all provide information about cognition and inattentiveness. There are other visual mental health function tests to detect cognitive impairments. These tasks can be used as visual mental health function assessments, that will be further described with reference to FIG. 14.

FIG. 2A, FIG. 2B, FIG. 3, FIG. 4A, and FIG. 4B illustrate examples of extended reality (XR) devices that can be used for implementing the method described in FIG. 1. All of these devices share the following attributes that were discussed with reference to FIG. 1:

(a) They are wearable;
(b) They comprise an eye imaging module (or modules);
(c) They comprise a display (or displays); and
(d) The data from these devices can be used for health condition intervention (step 899 in FIG. 1) or as input for control of a system (step 821 in FIG. 1).

Figure 2A:
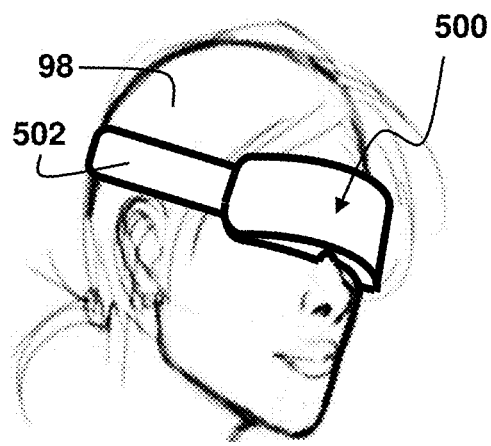
FIG. 2A shows a wearable virtual reality device for implementing the method of FIG. 1.
Figure 2B:
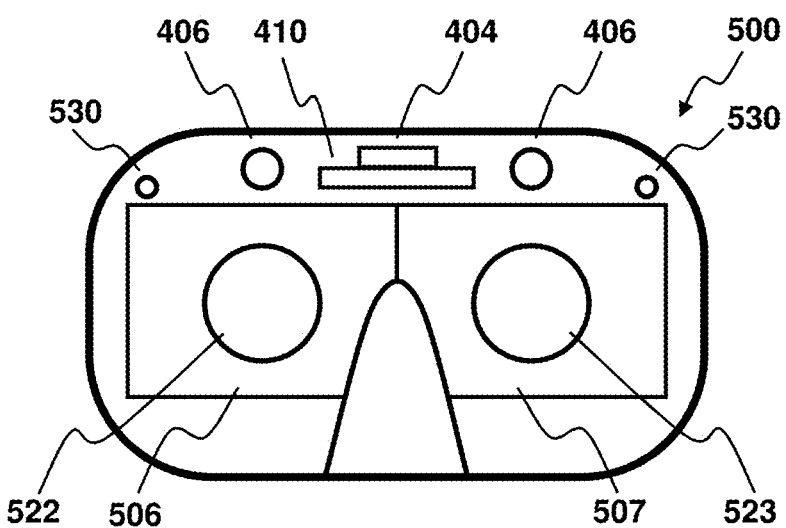
FIG. 2B shows a view of the inside of the virtual reality device of FIG. 2A.
Figure 3:
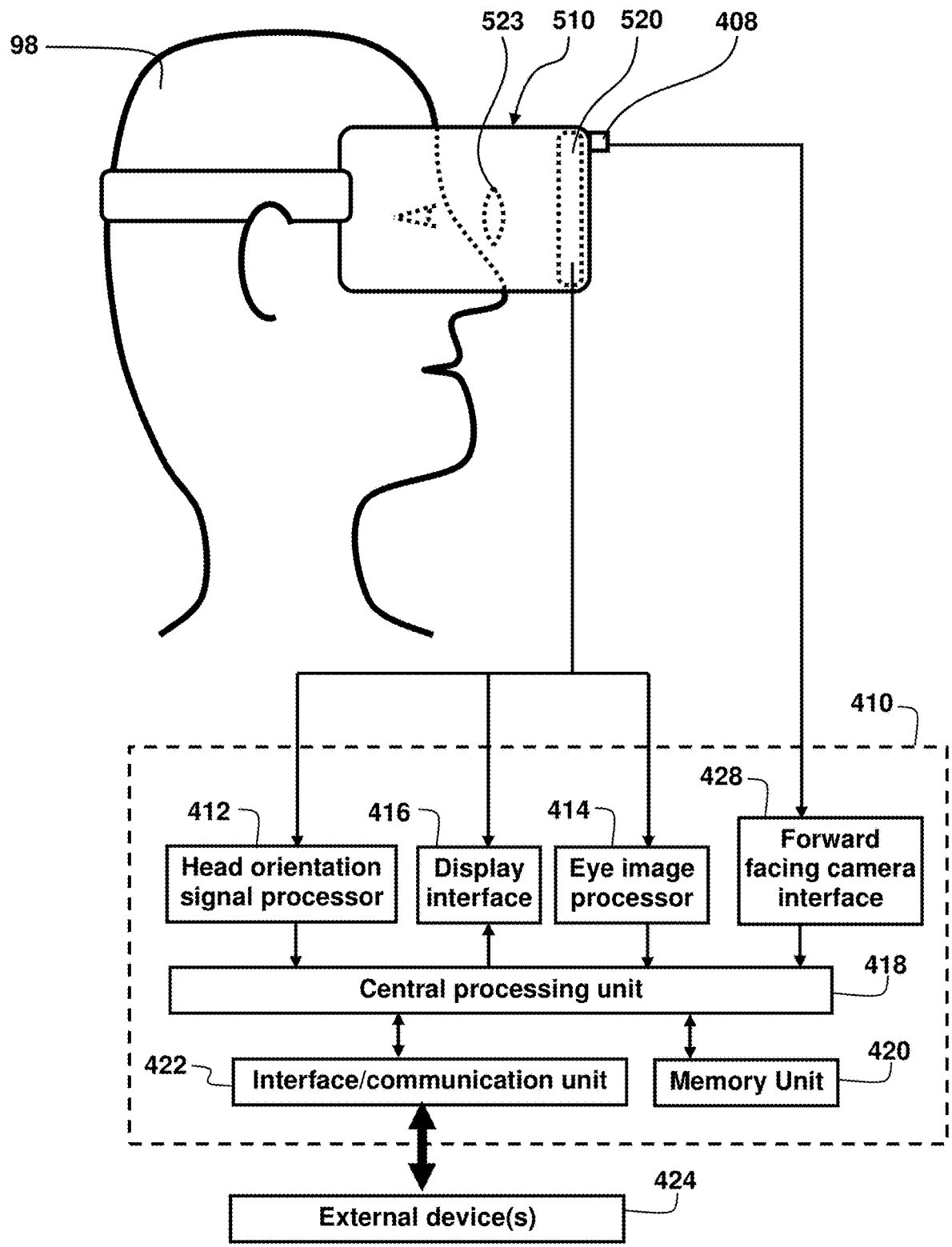
FIG. 3 is a side view of the virtual reality device of FIG. 2A, and associated electronics.

FIG. 2A, FIG. 2B, and FIG. 3 show virtual reality (VR) goggles embodiments of a wearable device for measuring human ocular parameters. FIG. 2A shows the VR goggles 500, attached to a person's head 98, with a strap or headband 502. FIG. 2B shows that the virtual reality goggles 500 can comprise a left virtual reality display 506 and a right virtual reality display 507. These displays 506 and 507 are opaque and the user is typically completely immersed in the scene being displayed. FIG. 2B also shows that the VR goggles can have a head orientation sensor 404, eye imaging device(s) 406 (of which there can be one for the left eye and one for the right eye), and an electronic module 410. For the person's eyes to be able to focus on the displays (506 and 507), there are typically two lenses 522 (left eye lens) and 523 (right eye lens) between the person's eyes and the displays, 506 and 507. Because the interior of the VR device 500 is not exposed to external light, there can be one or more illumination source(s) 530, to provide light that can be used by the imaging device(s) 406 to sense ocular parameters such as eye position, or pupil size, and/or eye or eyelid (e.g., eyeblink) motion or any of the other ocular parameters described in other parts of this document. The illumination source or sources 530, can use infrared, near infrared, or visible light. Ideally, the eye imaging sensor 406 would be below the upper lid margin of the user's eyelid to best capture the characteristics of the eye, and the illumination source 530 should be below the eye imaging sensor 406. Other attributes of the illumination source (light source) can include:

(a) The light source 530 may be positioned along an optical axis that is centered when the pupil is looking straight or off the optical axis.
(b) The light source 530, or sources can generate infrared (IR) light, short-wavelength infrared (SWIR), near-infrared light (NIR), NIR-filtered broadband light, visible light, light-emitting diodes (LEDs), red, blue, and green (RBG) lasers, diode lasers and/or fiber lasers.
(c) The light emitted by the light source 530 can be continuous or pulsed or used in any combination with the different light sources.
(d) The light source 530 can comprise a light collimator.
(e) The system can also scan different resolutions of infra-red light to different portions of the eye.

Referring specifically to the left and right eye imaging device(s) 406 in FIG. 2B, these eye imaging devices (more generally eye sensors) can be used for more than just the tracking of eye position and eye movement in response to head movement. The eye sensors 406 can also be used to perform the following functions:

(a) The eye sensors could be used to provide control information. For example, the position of one or both eyes (or the orientation or movement of the eyes and/or eyelids) could be used to determine which of a plurality of choices a user has selected in a menu of options presented on a display. This selection could be to change the scene being displayed to the user. This selection could be used to turn something on or off.
(b) The eye sensors could be used to image one or both retinas of the person, to capture anatomic characteristics of a retina, to capture motion and/or orientation of a retina, and/or to determine retina image stability and/or foveal fixation.

It should be noted that embodiments of the present invention can be implemented using video cameras for the imaging devices or imaging devices which are not video cameras. Examples of non-video camera eye imaging sensors can include opto-electrical transducers, photodiodes, photodetectors, and electromagnetic trackers. Embodiments of the present invention could also be implemented with the use of a virtual retinal display providing an image directly on the retina of the user's eye.

FIG. 3 shows wearable smartphone based virtual reality goggles 510, comprising a smartphone 520. These goggles 510, use the smartphone 520, to provide the display, the eye imaging device (in the form of a user-facing camera), and the head tracker functionality, and doing many or all of the functions of the electronic module. To help the person's eyes focus on the display of the smartphone 520, these virtual reality goggles further comprise one or two lenses 522 and/or 523, that sit between the eyes of the person's head 98, and the smartphone 520. In the embodiment shown in FIG. 3, the smartphone 520 can contain embedded software to perform all the necessary functions of measuring all eye movements and/or ocular functions as well as measuring head movements. As an example, head orientation and eye position and movements can be detected and measured to perform the ocular parameter measurements discussed in this document. Instructional signals, such as when to rotate the head while looking a visual target, can be random to prevent the subject from anticipating the timing, in the form of visual cues, auditory signals or a haptic signal. Calibration and other specific ocular parameters test measures can similarly be performed with the smart phone application. Data obtained can be logged and transmitted wirelessly to another smart device.

In the embodiment shown in FIG. 3, the smartphone 520 comprises the eye imaging module 406, head orientation sensor 404, and display or displays (506 and 507) that were shown in FIG. 2B. FIG. 3 also shows a forward-facing camera 408, which could be part of the smartphone 520 or could be a separate device. Similarly, the functions of an electronic module 410 could either be embedded as part of the smartphone 520, or these elements of the system could be separate items if a smartphone is not used, as is the case for the embodiment shown in FIG. 2B. The components in the electronics module 410 can comprise:
- (a) A forward-facing camera interface 428 that connects the forward-facing camera 408 to a central processing unit 418;
- (b) An eye image processor 214 that either connects to an eye imaging module (406 in FIG. 2B) or comparable functionality in the smartphone 520, while also working with the central processing unit 418;
- (c) A display interface 416 that either connects to the display or displays (506 and 507 in FIG. 2B) or comparable functionality in the smartphone 520, while also working with the central processing unit 418;
- (d) A head orientation signal processor 412 that either connects to the head orientation sensor (404 in FIG. 2B) or comparable functionality in the smartphone 520, while also working with the central processing unit 418;
- (e) A memory unit 420 connected to the central processing unit 418 for storing data and/or code; and
- (f) An interface/communication unit 422 configured for communicating with an external device or devices 424.

Figure 4A:
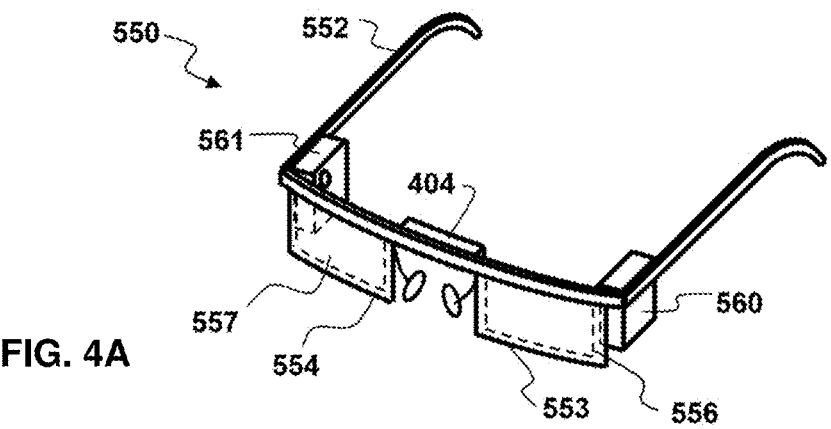
FIG. 4A is a wearable augmented reality device for implementing the method of FIG. 1.

FIG. 4A shows an eyeglasses embodiment of a wearable device for measuring human ocular performance 550 to determine human health. The eyeglasses device 550, is an example of an augmented reality (AR) device. This augmented reality (AR) device has many similarities with the virtual reality (VR) devices that were shown in FIG. 2A, FIG. 2B, and FIG. 3. The primary difference is that with AR, the user's view of an actual scene, is augmented with information provided the eyes of the wearer. The eyeglasses device 550 in FIG. 4A, could be electronically coupled to an electronic module (410 in FIG. 4B), and this electronic module 410 could be part of the eyeglass's device 550, or the electronic module 410, could be external to the eyeglass's device 550, and communicate through a wired or wireless connection. As shown in FIG. 4A, the eyeglasses device 550, comprises a spectacles frame 552, which is attaches the eyeglasses device 550 to a person's head. The eyeglasses device 550 also comprises a left eyeglass 553, and a right eyeglass 554. The left and/or right eyeglasses could be lenses, they could be clear windows, or they could be translucent windows. Also shown are a left display 556, and a right display 557. In the embodiment shown in FIG. 4A, the displays, 556, and 557, are see-through displays that are located between the left and right eyeglass, 553, and 554, and the eyes of the person. When the displays, 556, and 557, are in this location, it is not as obvious to an outsider that the device 550 is a wearable system for measuring ocular performance. The displays, 556, and 557, could also be external to the left and right eyeglasses 553, and 554. In another embodiment, the displays, 556, and 557, could be located within the eyeglass device, 554, and 555. There could be only one display, 556, or 557. The display could be off-bore and only visible in a person's peripheral vision, such as the embodiments shown in U.S. Pat. No. 9,075,249.

Further referring to FIG. 4A, the eyeglasses device can also comprise a head orientation sensor located in the bridge 404, a left eye imaging device 560, and a right eye imaging device 561. All these components can be connected similarly and, in any configuration, and combination to other embodiments described herein.

The embodiments shown in FIG. 7A can be considered augmented reality implementations. In these augmented reality devices, the display could be see-through or opaque. If it is opaque, it could cover part or all the field of view. If it is see-through or opaque and covers only part of the field of view, it could be in one eye or both eyes. If it is opaque and covers the entire field of view, it can only be in one eye. The augmented reality display(s) in these embodiments can provide an image of interest or a target for the user to focus on. This image of interest (or target) could be a circular object, such as a pool ball. This image of interest or target could be static (not moving) in the field of view, or it could be dynamic (i.e., moving in the field of view). In this document the visual element has the same meaning as the target visual element, visual target and/or target element.

Figure 4B:
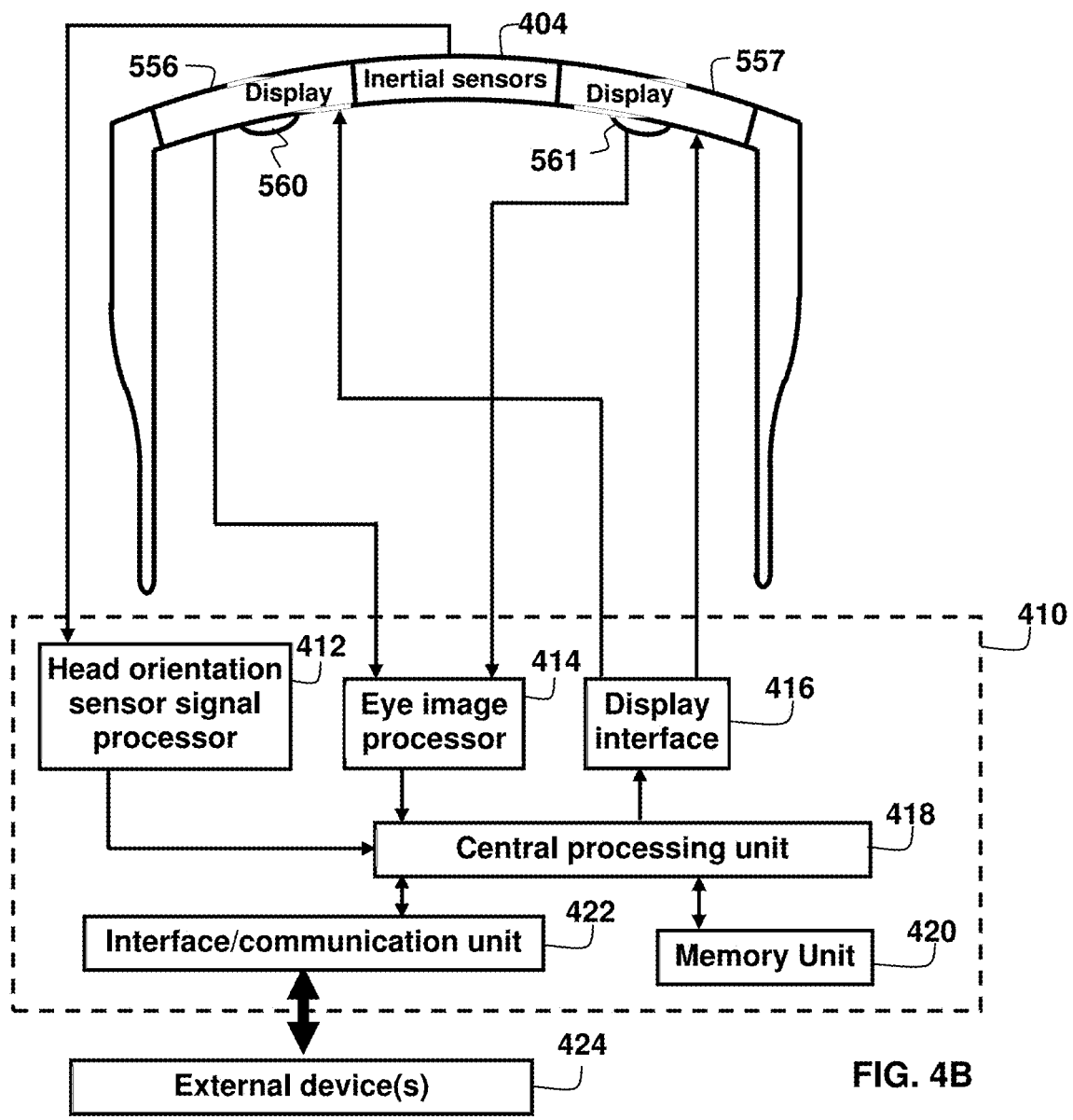
FIG. 4B is a top view of the device of FIG. 4A, and associated electronics.

FIG. 4B shows a top view of an augmented reality or virtual reality system that also includes the main elements that were shown in FIG. 2B, FIG. 3 and FIG. 4A, including a head orientation sensor 404, a left display 556, a right display 557, a left eye imaging device 560, a right eye imaging device 561, an electronic module 410, an orientation signal processor 412, an eye image processor 414, a display interface 416, a central processing unit 418, a memory unit 420, an interface/communication unit 422, and an external device 424. An alternate embodiment can include a forward-facing camera 408, like that previously described in FIG. C, that communicates with a forward-facing camera interface 428, in the electronic module 410. The forward-facing camera 408, can be responsive to the eye sensors to measure the ocular performance.

Figure 5:
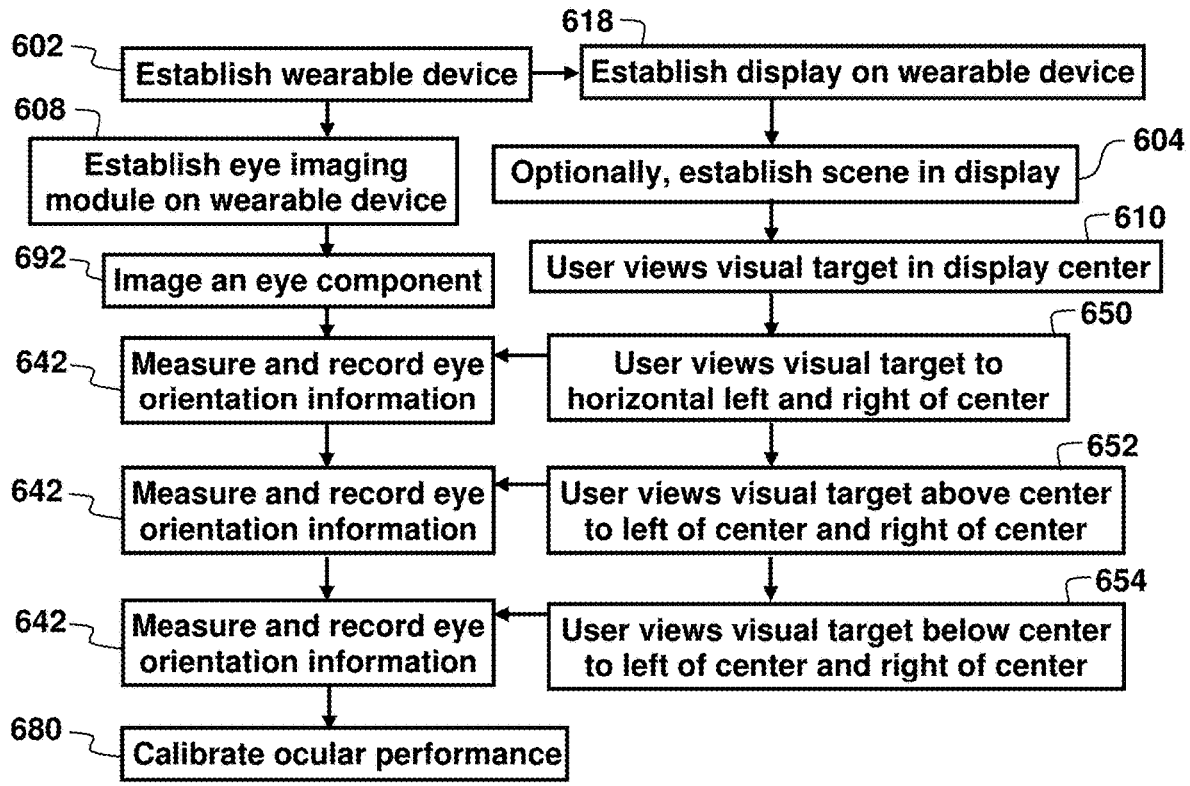
FIG. 5 shows a method for calibrating ocular performance.

FIG. 5 shows an example of an ocular performance calibration method that can be implemented using the generalized method described in FIG. 1 and using an extended reality (XR) device of the type that was described with reference to FIG. 2A, FIG. 2B, FIB 3, FIG. 4A, and FIG. 4B. This method-comprises the following configuration and steps:
1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. The user views a visual target in the center of the scene 610.
4. The user then views a visual target to the left and right of center 650, while eye orientation information is recorded 642.
5. The user then views a visual target positioned superiorly (i.e., above the center of the scene) and to the left and right of center 652, while eye orientation information is recorded 642.
6. The user then views a visual target positioned inferiorly (i.e., below the center of the scene) and to the left and right of center 654, while eye orientation information is recorded 642.

7. This measured and recorded eye orientation information at a plurality of times 642 is then used to calibrate ocular performance 680.

In the assessments of ocular performance, described herein, it should be understood that the viewed visual target can represent a computer-generated virtual target positioned in the physical environment. The visual target may also be represented by normal visual targets as viewed in the field of activity or play, such as viewing the football, the helmet of another player, a piece of another player's uniform, a familiar object relative to the person's activity, or viewing a part of person's body. The ocular parameter assessment can use moving, rotating, or stationary visual elements or targets and measurements can be made in a very brief period of time (e.g., seconds) to assess the human health condition or human performance.

Figure 6:
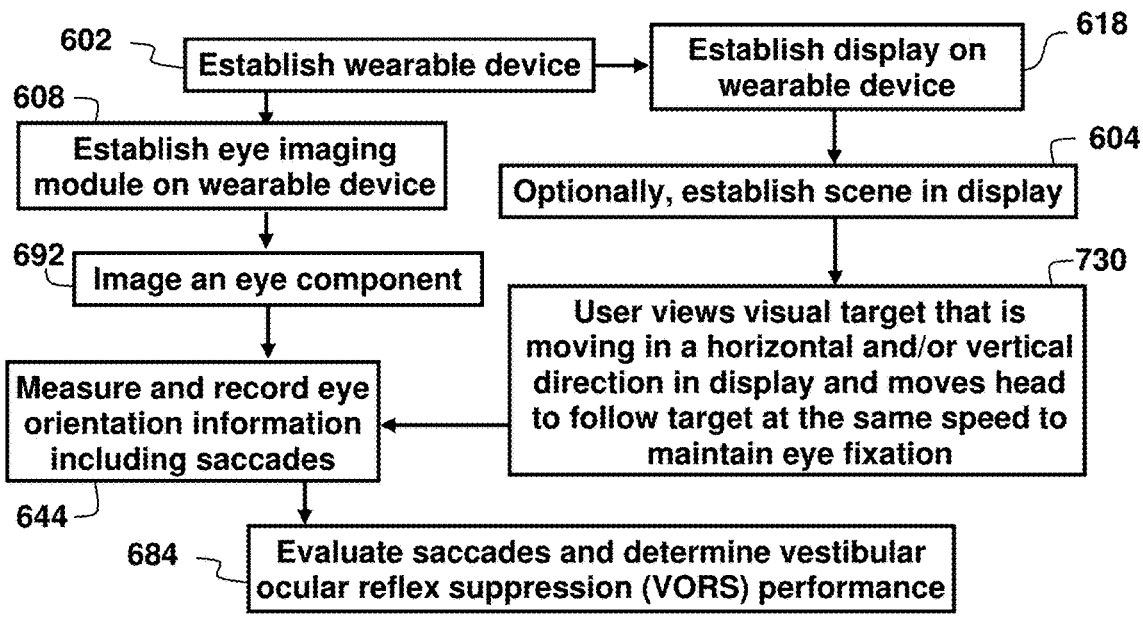
FIG. 6 is a method for saccade and vestibular ocular reflex suppression determination.

FIG. 6 shows an example of a method for evaluating saccades and determining vestibular ocular reflex suppression (VORS) performance. This example can be implemented using extended reality (XR) devices, including but not limited to, the systems and devices illustrated in FIG. 2A, FIG. 2B, FIG. 3, FIG. 4A, and FIG. 4B. It is a specific application of the generalized method of FIG. 1. This method comprises the following configuration and steps:
1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. The user views a visual target that is moving in a horizontal and/or vertical direction in the display and moves head to follow the visual target at the same speed to maintain eye fixation, as shown at step 730, while eye orientation information, including saccades, is measured as shown at 644.
4. This is then used to evaluate saccades and determine vestibular ocular reflex suppression performance, as shown at step 684.

In one embodiment, the saccades and vestibular ocular reflex suppression info 684 could be used to determine a behavioral health condition, such as substance use.

Figure 7:
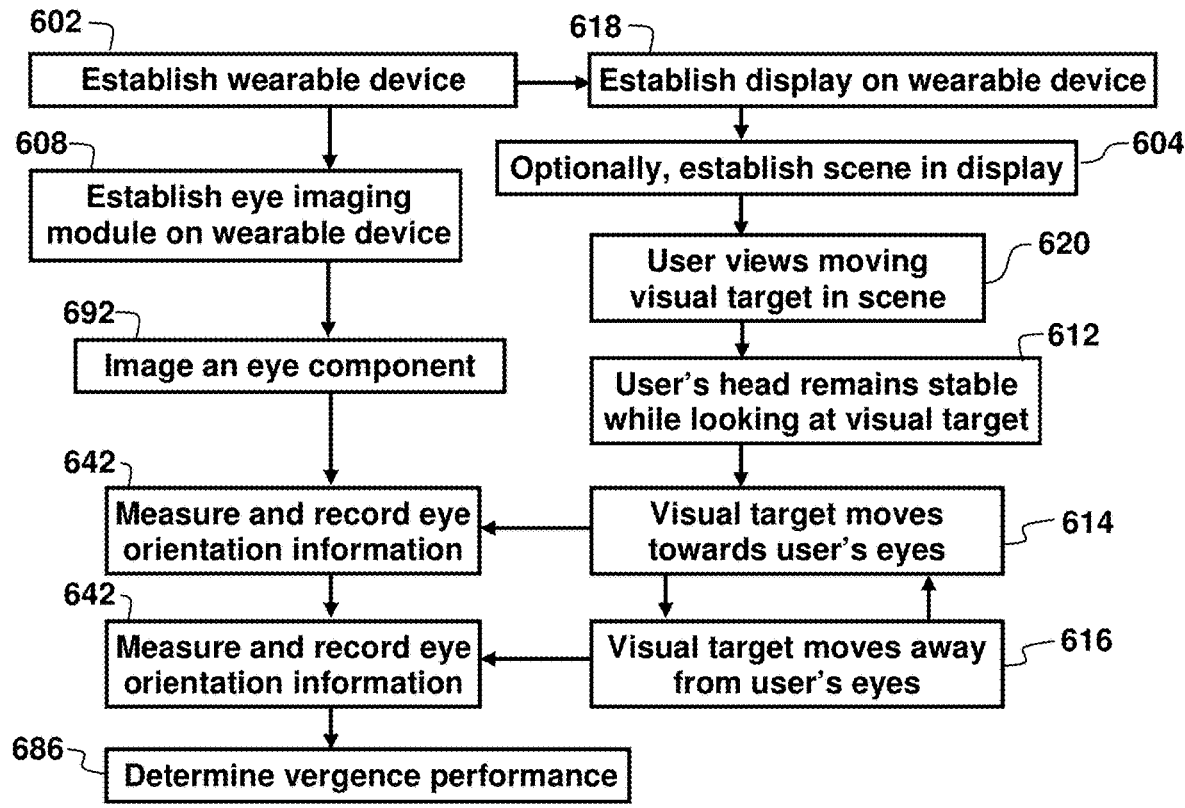
FIG. 7 shows a method for determining vergence performance.

FIG. 7 shows an example of a vergence measurement method that can be implemented using the generalized method described in FIG. 1 and using an extended reality (XR) device of the type that was described with reference to FIG. 2A, FIG. 2B, FIB 3, FIG. 4A, and FIG. 4B. This method-comprises the following configuration and steps:
1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. The user views a moving visual target in the scene 620.
4. The user's head remains stable while looking at this visual target as shown at 612.
5. The visual target then moves towards the user's eyes 614, while eye orientation information is recorded 642.
6. The visual target then moves away from the user's eyes 616, while eye orientation information is recorded 642. This process can be repeated.
7. This measured and recorded eye orientation information at a plurality of times 642 is then used to determine vergence performance 686.

In one embodiment, information from vergence performance 686, could be used to assess neurologic health conditions, such as traumatic brain injury.

Figure 8:
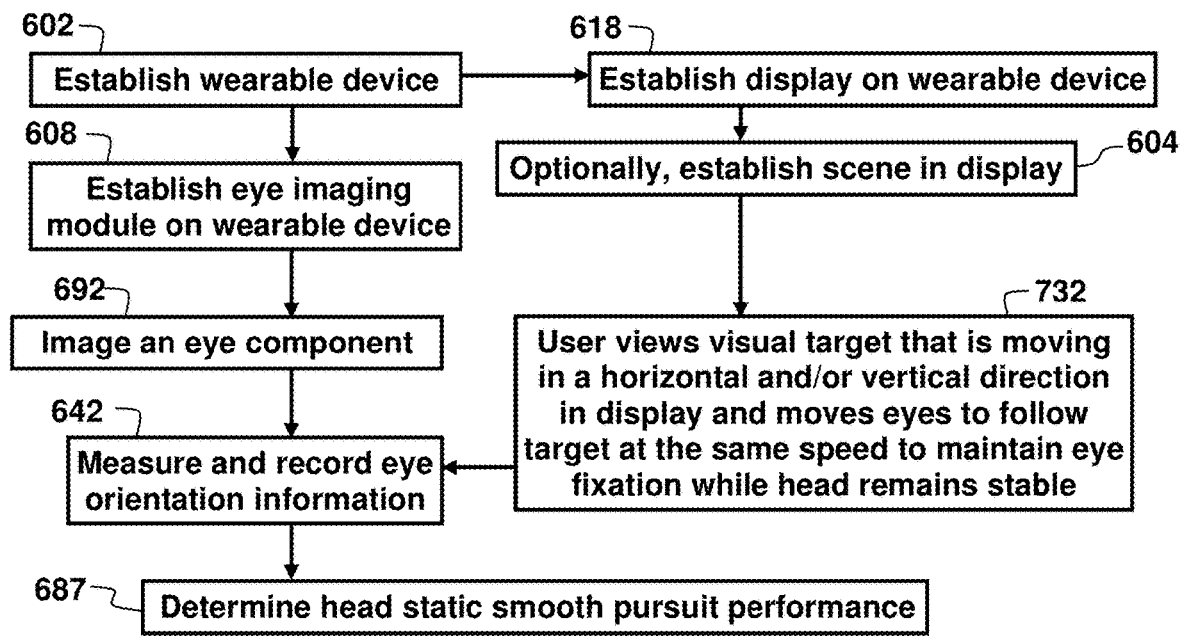
FIG. 8 shows a method for determining head static smooth pursuit performance.

FIG. 8 shows an example of a head static smooth pursuit performance measurement that can be implemented using the generalized method described in FIG. 1 and using an extended reality (XR) device of the type that was described with reference to FIG. 2A, FIG. 2B, FIB 3, FIG. 4A, and FIG. 4B. This method-comprises the following configuration and steps:
1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. The user views a moving visual target that is moving in a horizontal and/or vertical direction in the display and moves eyes to follow the target at the same speed to maintain eye fixation while the head remains stable, as shown at step 732, as eye orientation information is measured and recorded 642.
4. This comparison of the movement of the visual target (from 732) and measured eye orientation (from 642) is then used to determine head static smooth pursuit performance 687.

In one embodiment, information of head static smooth pursuit performance 687 could be used to determine mental health conditions, such as a cognitive impairment.

Figure 9:
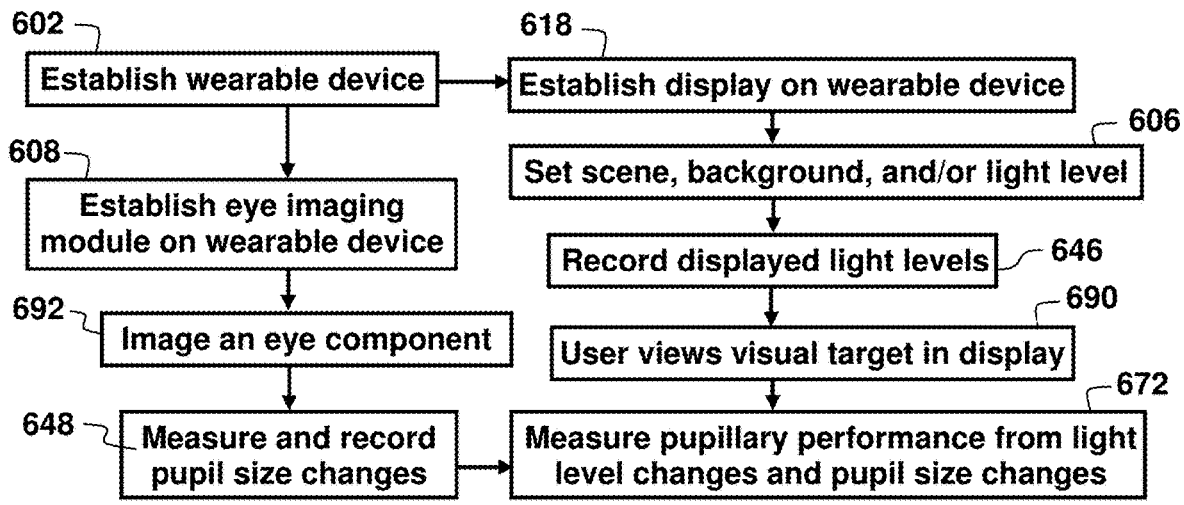
FIG. 9 shows pupil calibration and performance measurement method.

FIG. 9 shows an example of a pupil performance measurement method that can be implemented using the generalized method described in FIG. 1 and using an extended reality (XR) device of the type that was described with reference to FIG. 2A, FIG. 2B, FIB 3, FIG. 4A, and FIG. 4B. This method-comprises the following configuration and steps:
1. A wearable device 602, that comprises an eye imaging module 608 is established. This is used to image an eye component 692.
2. A display is established in the wearable device 618, and a scene, background, and/or light level is presented on the display 606. Alternatively, like that described in FIG. 1, the visual target can be viewed overlying the scene of a normal physical environment.
3. The light levels on the display are recorded 646 and the user is instructed to view a visual target that is part of the information presented on the display 690.
4. The eye imaging module 608 is used to image an eye component 692 to specifically measure and record pupil size changes as shown at step 648.
5. The light level information from step 646 is then combined with the pupil size change information from step 648 to measure pupillary performance, as shown at step 672.

In one embodiment, information from measurement of pupil size changes 672 could be used to determine a physiologic impairment 808, as seen in FIG. 1, such as with the assessed health condition of fatigue. The assessed health condition 698 could be used for control input 821, such as disabling a vehicle.

Figure 10:
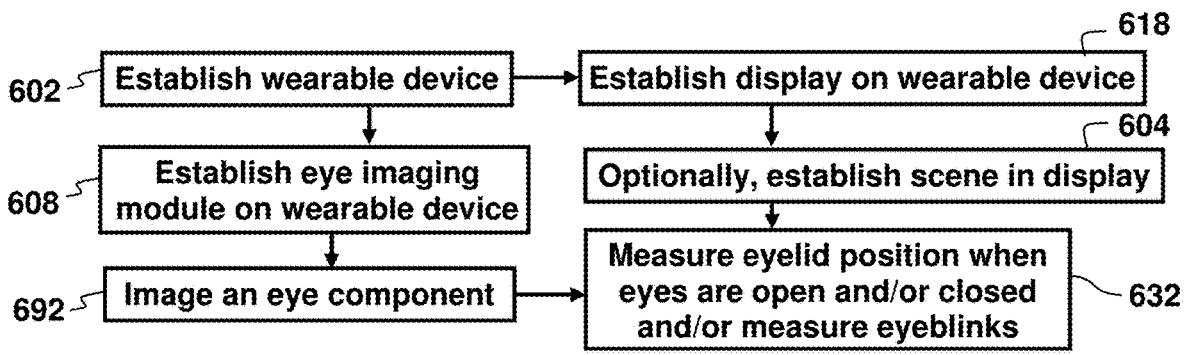
FIG. 10 shows a method for measuring eyeblinks.

FIG. 10 shows an eyeblink measurement method that can be implemented using the generalized method described in FIG. 1 and using an extended reality (XR) device of the type that was described with reference to FIG. 2A, FIG. 2B, FIB 3, FIG. 4A, and FIG. 4B. This method-comprises the following configuration and steps:
1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. For this measurement, the eye component that is measured is the eyelid and the measurement at step 632 is information, such as (a) when the eyes are open and or closed, and/or eyeblinks.
4. The eyelid measurements from 692 can then be converted to eyeblink measures in step 632. Examples of eyeblink measures can include eyeblink duration, interblink interval, blink rate (frequency), amplitude, velocity, latency, asymmetry between the eyes and completeness.
5. This eyeblink measurement 632 can then be used for a variety of purposes, as shown at steps 899 and 821 in FIG. 1.

In one embodiment, information from measurement of eyeblinks 632 could be used to determine a behavioral health condition impairment 805, as seen in FIG. 1, such as with the assessed health condition of substance use impairment. The assessed health condition 698 could be used for control input 821, such as disabling a vehicle.

In an alternative embodiment of FIG. 10, the extended reality (XR) device might not be worn. An example could be a motorcycle windshield, automobile windshield, boat windshield, or aircraft windshield. In this instance, FIG. 10 can illustrate an example of how the measurement of eyeblinks at step 632, could be used as input to the control of a system 821, such as controlling a vehicle.

Figure 11:
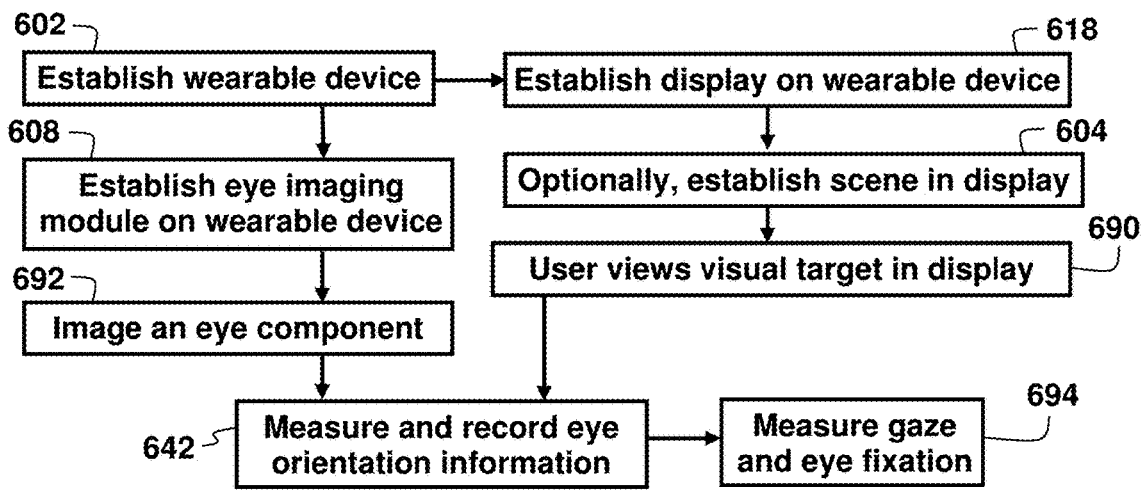
FIG. 11 shows a method for measuring gaze and eye fixation.

FIG. 11 shows an example of a method for measuring gaze and eye fixation measurement as part of the generalized method described in FIG. 1, using an extended reality (XR) device of the type that was described with reference to FIG. 2A, FIG. 2B, FIB 3, FIG. 4A, and FIG. 4B. This method-comprises the following configuration and steps:
1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. The eye imaging module 608 measures eye movement and/or eye position and/or eye orientation 642.
4. The user views a visual target in the display 690 and this visual input is processed in the subject's visual cortex.
5. The subject's oculomotor system activates extraocular muscles. The planned eye movement is executed through the activation of the extraocular muscles, leading to a shift in gaze.
6. Extraocular muscles shift eyes to gaze the area of interest toward a specific point of interest and can encompass various movements.
7. The eye imaging module images an eye component 692 to measure and record eye position, eye movement, and or eye orientation (step 642) while the user is viewing the visual target in the natural scene as was described for step 690.
8. The eye movement brings the gaze to a specific point in the visual scene, and the eyes stabilize to maintain eye fixation on that point.
9. A processor in the system uses the recorded eye orientation information 642 to measure gaze (where a person is looking) and eye fixation (ability to continue to look at this same visual target) 694.

Note that gaze and eye fixation can be measured by using infrared (IR) light to illuminate the eyes. Infrared light reflects off the cornea creating a glint on the eye's surface, which can determine the direction of gaze. The IR light could come from a source attached or embedded in the eye imaging module, or the IR source could be separate from the eye imaging module. Micro-opto-electro-mechanical systems (MOEMS) sensors can be used to direct and control IR light emission. The captured images can then be processed to extract information about the position of the pupils, corneal reflections, or other features indicative of gaze direction. Alternatively, video cameras could capture images or video of the user's eyes and these video cameras could include multiple sensors for better accuracy. Sensors can monitor changes of eye position to measure gaze and eye fixation.

Figure 12:
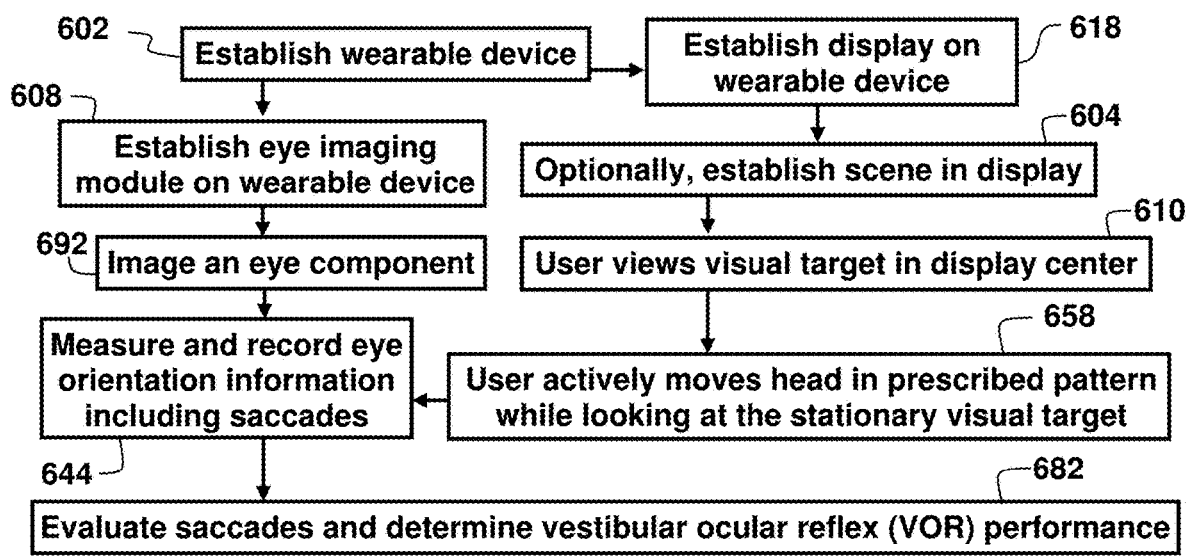
FIG. 12 show a method for saccade and vestibular ocular reflex determination.

FIG. 12 shows an example of a method for evaluating saccades and determining vestibular ocular reflex (VOR) performance as part of the generalized method described in FIG. 1, using an extended reality (XR) device of the type that was described with reference to FIG. 2A, FIG. 2B, FIB 3, FIG. 4A, and FIG. 4B. This method comprises the following configuration and steps:
1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. The user views a visual target in the display center 610.
4. The user actively moves head in a prescribed pattern while looking at the stationary target 658, while eye orientation information, including saccades, is measured 644.
5. A processor uses the recorded eye orientation and saccade information 644 to evaluate saccades and determine vestibular ocular reflex (VOR) performance 682.

Figure 13:
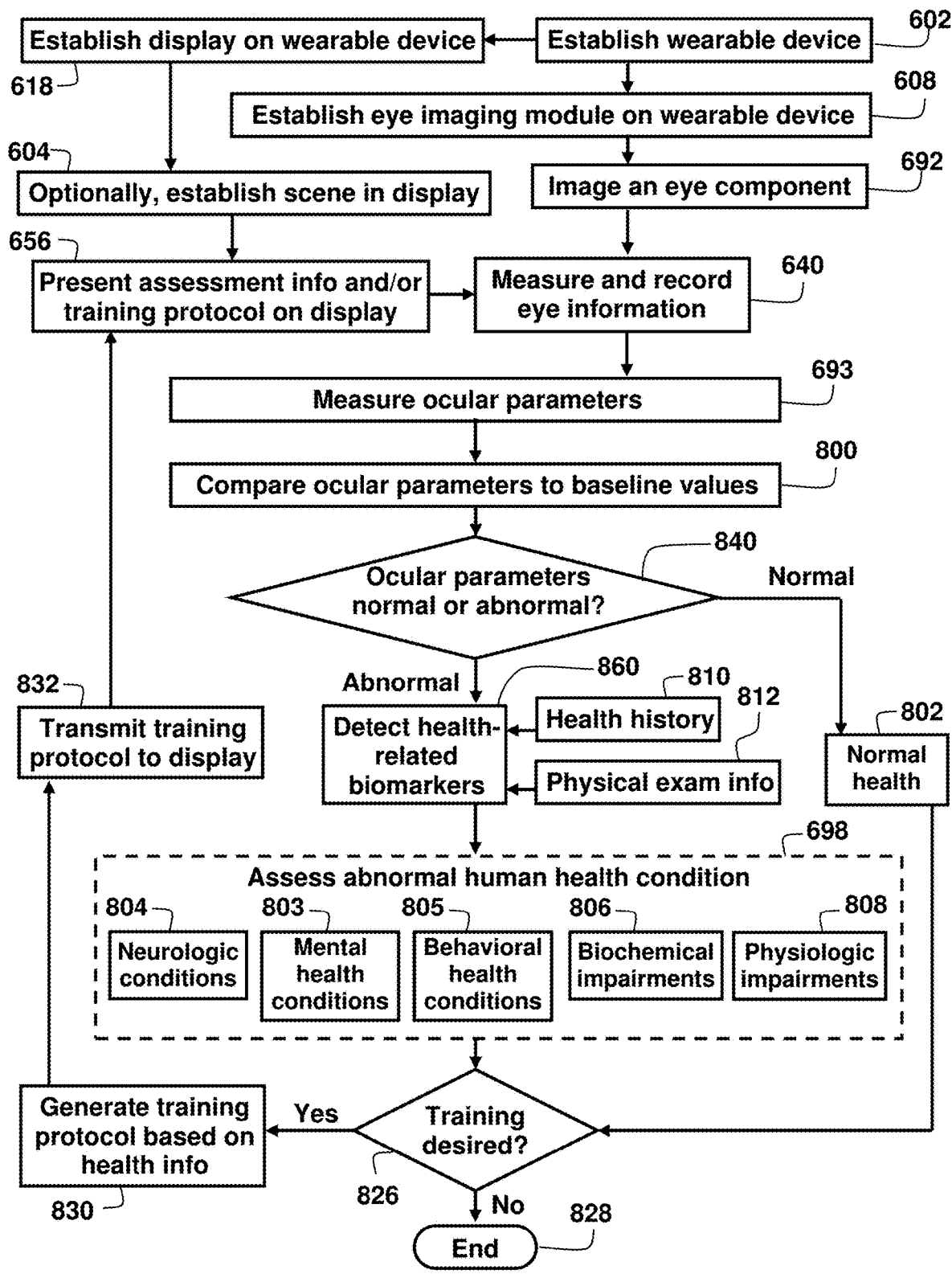
FIG. 13 shows a training, rehabilitation, and/or performance enhancement method.

FIG. 13 shows an example of a training method that can be implemented using the generalized method described in FIG. 1 and using an extended reality (XR) device of the type that was described with reference to FIG. 2A, FIG. 2B, FIB 3, FIG. 4A, and FIG. 4B. This method-comprises the following configuration and steps:
1. A wearable device 602, that comprises an eye imaging module 608 is established. This is used to image an eye component 692.
2. A display is established in the wearable device 618, and optionally a scene is established 604 on the display 618.
3. The display 618 is used to present assessment information and or training protocols, as shown at step 656. Alternatively, like that described in FIG. 1, the visual target can be viewed overlying the scene of a normal physical environment.

4. Eye information is measured and recorded, as shown at 640. This could be any of the types of eye information described in this document.
5. This measured eye information from step 640 can be used to measure any of the ocular parameters that have been discussed herein, as shown at step 693.
6. These ocular parameters 693 could be compared to baseline values 800 to determine if these ocular parameters are abnormal, as shown at step 840.
7. If ocular parameters indicate normal health 802, the process can move directly to a decision box to determine if training is desired 826.
8. If ocular parameters are abnormal (from 840), these parameters could be combined with health history 810 and physical exam info (812) to detect health related biomarkers, as shown at step 860.
9. These biomarkers from step 860 could then be used to assess a human health condition 698, which could be a neurologic condition 804, a mental health condition 803, a behavioral health condition 805, a biochemical impairment 806, or a physiologic impairment 808, as described in other parts of this document.
10. If the ocular parameters from 698 indicate an abnormal condition, the process can move to the same decision box described previously for normal health, shown at 826.
11. If training is not desired at step 626, the process ends at step 828.
12. If training is desired, a protocol can be generated at step 830, and this protocol can be based on the health information from 698.
13. The training protocol from 830 can be transmitted to the display 832 and presented on the display, as shown at 656, allowing the cycle to be repeated.

Further referring to FIG. 13, the human subject's health condition 698 could be treated with visual-oculomotor (VO) rehabilitation if an abnormality of any ocular parameter is detected. Visual training with repeat ocular parameter methods, can provide an above normal level of eye fixation for performing athletic or occupational activities. While VO rehabilitation is often referred to as restoration of a visual acuity impairment, in this document and embodiments it also refers to performing specific visual rehabilitation tasks required to restore ocular parameters to normal, which were found to be previously abnormal. If an abnormality is detected with one or more of the specific ocular parameters being tested, a specialized program can be viewed. For example, if an abnormal VO impairment is detected with a TBI (traumatic brain injury) or other impairment, the individual can receive a VO rehab program, like the method shown in FIG. 1, but in repetitive fashion, in different directions and with optimizing the visual elements to enhance visual fixation. Effective rehabilitation interventions initiated early after a traumatic brain injury has been shown to enhance the recovery process and minimize the functional disability. The return of normal ocular parameters can provide a precise risk assessment to guide the determination for return to play activities with high performance predictability, based on the ability for return of measured eye movement responses to achieve normal values.

With reference to step 830 in FIG. 13, the training protocol (or training information) is responsive to the ocular parameter measurement from step 693, compared to baseline values (normal values) from step 800, which allow the detection of one or more abnormal ocular parameter(s) 840. The abnormal ocular parameter 840, in combination with the health history 810 and physical exam information 812 can establish the health-related biomarkers 860, which in turn allow the assessment of health status 698. With the knowledge of knowing the health condition 698, it can be determined if rehabilitative training 826 is necessary, enhancement of visual-oculomotor training is desired, or no training is needed or desired. If training is desired, a protocol based on health condition 698 information can be generated at step 830. The detected health condition will determine the training and rehab protocol, as the specific training and rehab protocol is responsive to the recorded eye information. The specific protocol for each abnormality, such as those seen in the table below, can be stored in an app or on the internet cloud, and automatically generated in the display for use.

The following table illustrates more specifically how the abnormal ocular parameters from step 840 can be used to generate the training protocols. The table below gives an example of the behavior of the visual target and instructions for the individual to follow.

| Abnormal Ocular Parameter | Generated training protocol |
| --- | --- |
| Abnormal saccades | Eye fixation stabilization training, which can be combined with balance training to reduce saccadic activity and improve saccade accuracy:<br>a. Visual target is focused upon to reduce microsaccades.<br>b. Individual views visual target, ensuring that head is aligned with target, then views target to left, then right. This can be repeated at different speeds.<br>c. Individual view visual target, ensuring that head is aligned with target, then views target above, then below. This can be repeated at different speeds.<br>d. Balance training tasks, such as standing, or walking can be added while the subject repeats the above tests. |
| Abnormal vergence | Eye fixation stabilization training exercises, which can be combined with balance training:<br>a. Individual views a visual target as the target is moved toward the nose.<br>b. The target continues to move toward the nose until the double vision occurs. At this point, the target is moved away until the double vision resolves. The distance of the visual target moving away from the nose can vary.<br>c. The target is held stationary for a few seconds while the subject focuses on the visual target and the training exercise is repeated.<br>d. Individual can work on improving this threshold by achieving a closer distance from the nose each time. |

| Abnormal Ocular Parameter | Generated training protocol |
| --- | --- |
| | e. Balance training tasks can be added, such as doing the above exercise while standing with feet together, split stance (one foot in front of the other), or on one foot. |
| Abnormal head static smooth pursuit | Eye fixation stabilization training exercises, which can be combined with balance training:<br>a. Individual views a visual target as the target is in motion, with head remaining stable.<br>b. The target in this exercise can move in any direction and at different speeds.<br>c. Individual then focuses on two separate targets, alternating between them in the horizontal plane and/or the vertical plane.<br>d. Individual uses quick eye movements to move the visual focus from target to target in a zig-zag pattern.<br>e. Individual can also focus on visual target motion of a bouncing ball or other visual target object. |
| Abnormal vestibular ocular reflex suppression | Eye fixation stabilization training exercises:<br>a. Individual focuses on a stationary object while moving the head slowly side to side, up and down, or in circular motions.<br>b. Individual moves the head while maintaining focus on a target. This includes moving the head while following a moving object with the eyes. |
| Abnormal dynamic visual acuity | Eye fixation stabilization training:<br>a. Individual maintains visual fixation on an enhance visual target while moving head horizontally and vertically.<br>b. Individual reads letters written on moving visual targets.<br>c. Individual reads smallest letter displayed while head is in motion. |
| Abnormal pupil performance | Pupil control is balanced between sympathetic and parasympathetic nervous system:<br>a. Individual alternates between rest and relaxation of eyes.<br>b. Avoid direct light in eyes.<br>c. Gradual exposure to vaying light conditions with biofeedback. |
| Abnormal eyeblinks | a. Individual practices conscious and controlled training of firm blinks.<br>b. Practice blink rate and alter incomplete blinks. |
| Abnormal vestibular ocular reflex (VOR) | Eye fixation exercises:<br>a. Individual focuses on a visual target as target moves side-to-side, up-down, or diagonally while keeping the head still.<br>b. Individual views two separate targets and quickly shifts the eyes between them while keeping the head still.<br>c. Individual keeps eyes fixed on a stationary target while moving the head side-to-side, up-down, or rotating it.<br>d. Individual moves the head and eyes together in the same direction while fixating on a moving target.<br>e. Individual moves the head in one direction while moving their eyes in the opposite direction while maintaining fixation on the visual target. |

Further referring to the table above, it should be noted that dynamic activity (walking or other movement) could be added to any of the above training protocols. Such requested movements could be performed at a prescribed metronomic pace. The above training protocols could be performed by the individual multiple times per day. Additionally, visual targets viewed could be enhanced to provide improved eye fixation ability and minimize saccade activity.

FIG. 14 shows an example of a method for determining cognitive impairment that can be implemented using the generalized method described in FIG. 1 and using an extended reality (XR) device of the type that was described with reference to FIG. 2A, FIG. 2B, FIB 3, FIG. 4A, and FIG. 4B. This method-comprises the following configuration and steps:

1. A wearable device 602, that comprises an eye imaging module 608 is established. This is used to image an eye component 692.
6. A display is established in the wearable device 618, and optionally a scene is established 604 on the display 618. Alternatively, like that described in FIG. 1, the visual target can be viewed overlying the scene of a normal physical environment.
2. While a user views a natural scene 690, eye information is measured and recorded, as shown at 640.
3. This measured eye information from step 640 can be used to measure any of the ocular parameters that have been discussed herein, as shown at step 693.
4. These ocular parameters 693 could be compared to baseline values 800 to detect abnormal ocular parameters 840.
5. The abnormal ocular parameters 840 could be combined with internal body medical imaging 846 (such as CT scans, MRI, ultrasound, etc.), the results of mental health function tests 842, and health history information 810 to detect health related biomarkers, as shown at step 860.
6. The biomarkers 860 could then be used to assess cognitive impairment 894.
7. Finally, this data can be used for health condition intervention, as shown at 899.

Regarding step 842 in FIG. 14, there can be numerous visual mental health function tests. Examples include:

(a) Visual attention assessment can be achieved by measuring the duration of sustained attention of an individual's eye fixation on a specific visual target over time.

(b) Visual navigation can be measured by quickly identifying a visual target of interest, and the individual's ability to execute smooth pursuit of eyes while following the target along different paths, and quickly identifying visual targets. The reaction time, accuracy, and errors are also recorded.

(c) Visual perception can be measured by an individual's ability to focus on a selected visual target and screen out or ignore irrelevant objects, and associations between the objects.

(d) Visual search can be measured by an individual's ability to locate and identify a specific visual target within a scene, which may be complex with other objects. The visual target of interest could be an object related to the activity the individual is engaged in and the scene can be comprised of visual stimuli of varying complexity. The reaction time, accuracy, and errors can then be recorded.

FIG. 15 shows how health condition differences can be categorized to determine pharmacological intervention effects on measures of ocular parameters for individuals having neurologic conditions, biochemical impairments, and/or physiologic impairments. This method can be implemented using an extended reality (XR) device of the type that was described with reference to FIG. 2A, FIG. 2B, FIB 3, FIG. 4A, and FIG. 4B. This method comprises the following configuration and steps:

1. A wearable device 602, that comprises an eye imaging module 608 is established. This is used to image an eye component 692.
2. A display is established in the wearable device 618, and optionally a scene is established 604 on the display 618. Alternatively, like that described in FIG. 1, the visual target can be viewed overlying the scene of a normal physical environment.
3. The user is instructed to view a visual target that is moving in a horizontal and/or vertical direction in a natural scene and moves eyes to follow target at the same speed in order to maintain eye fixation while the head remains stable, as shown at 732. Eye information is measured and recorded while this is going on, as shown at step 640.
4. The eye information from step 640 is then combined with information about the natural scene from 732, to measure ocular parameters, as shown at step 693.
5. These ocular parameters 693 could be compared to baseline values 800 to detect if the ocular parameters 840 are abnormal.
6. If the ocular parameters from step 840 indicate normal health 802, the process ends, as shown at 828.
7. If the ocular parameters from step 840 are abnormal, this information can be combined with physical exam information 812 and health history information 810 to detect health related biomarkers, as shown at step 860.
8. The biomarkers 860 could then be used to assess a human health condition 698. In this case, a neurologic condition 804, biochemical impairment 806, or physiologic impairment 808, could be identified. This method is configured for assessing a pharmacologic intervention in response to the assessed human health condition.
9. As shown at decision 722, if health is normal, the process ends 828. If health is not normal, a pharmacologic intervention could be made, as shown at step 720, and the process described above could be repeated.
10. If pharmacologic intervention 720 is used for an abnormal health condition 698, then the process of measuring the ocular parameters 693 can be repeated at step 714 to determine if the ocular parameters are still abnormal or normal 840. If there are no further abnormal ocular parameters, it would indicate normal health 802 and the process ends at 828. If an abnormal ocular parameter persists with the related health biomarker 860, further assessment 722 can be made about terminating the drug and ending the process 828 or continuing with pharmacologic intervention 720.
11. This could be with the same drug or different drug therapy and the process can be repeated 714 as often as necessary to assess pharmacologic intervention with measurement of ocular parameters 693 to determine the status of the health condition as necessary.

Further referring to FIG. 15, in one embodiment if a neurologic condition is determined to be abnormal and pharmacological therapy is determined to be necessary or indicated, the technology described herein can be used to assess efficacy of administered drug therapy. The assessed abnormal health condition could even be obtained from accumulation of stored health-related biomarker data over time in the cloud, which when detected for an abnormality, using artificial intelligence, could automatically generate an electronic pharmacological prescription. This therapeutic intervention could then be more objectively assessed.

FIG. 16 shows an immersive system health assessment system 400 that uses an immersive external display 430 and an external eye sensor 407, to test the health of a human subject 98, without using any wearable components. The immersive system 400 can perform many of the same health procedures as the systems shown in FIG. 2A, FIG. 2B, FIG. 3, FIG. 4A, and FIG. 4B without having head-worn components by providing an immersive environment using a high-resolution two-dimensional display 430 facilitating a wide field of view. In one embodiment, this field of view can extend at least 45 degrees off bore to provide a 90-degree field of view. In another embodiment, this field of view could extend at least 60 degrees off bore to provide a 120-degree field of view. The external display 430 shown in FIG. 16 is a flat screen display. In another embodiment, this external display 430 could be a curved display. This curved display could provide a 90-degree, 120-degree, or 180-degree field of view. The immersive display 430 shows a scene, which in FIG. 16 comprises three trees and a dog. This scene could be any scene that works well for the health assessment being made. It could be a static scene or a moving scene. Also shown on the display 430 is a target 438. In the embodiment shown, this target 438 is a triangle, which helps distinguish it from the scene. Most typically, the target would be a colored dot. The external eye sensor 407 in the embodiment shown in FIG. 407 is a webcam. This external eye sensor can be any eye sensor 407 described in this document or capable of being understood by anyone skilled in the art.

Figure 17:
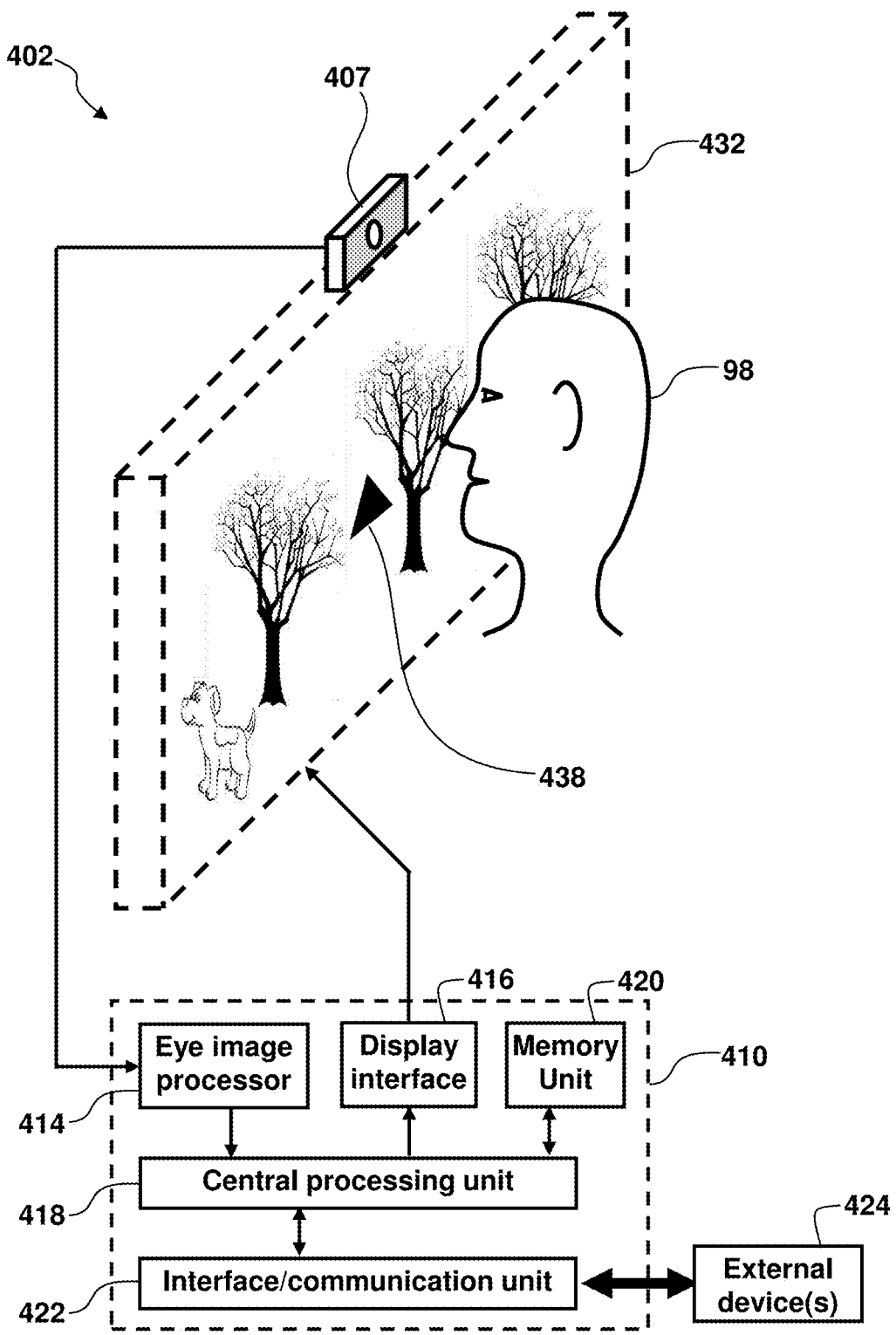
FIG. 17 is a system similar to FIG. 16 that uses a three-dimensional display.

FIG. 17 shows an immersive system similar to FIG. 16, the difference being that the immersive health assessment system 402 of FIG. 17 uses a three-dimensional display 432, instead of the two-dimensional immersive display shown at 430 in FIG. 16. The three-dimensional display 432 shown in FIG. 17 can be any three-dimensional display capable of being understood anyone skilled in the art, including but not limited to a stereographic display, a lenticular display, a volumetric display, and a holographic display. The scene on the three-dimensional display 432 can be similar to the scene shown earlier. The target 438 and external eye-imaging module 407 for testing the human subject 98 can also be similar.

Figure 18:
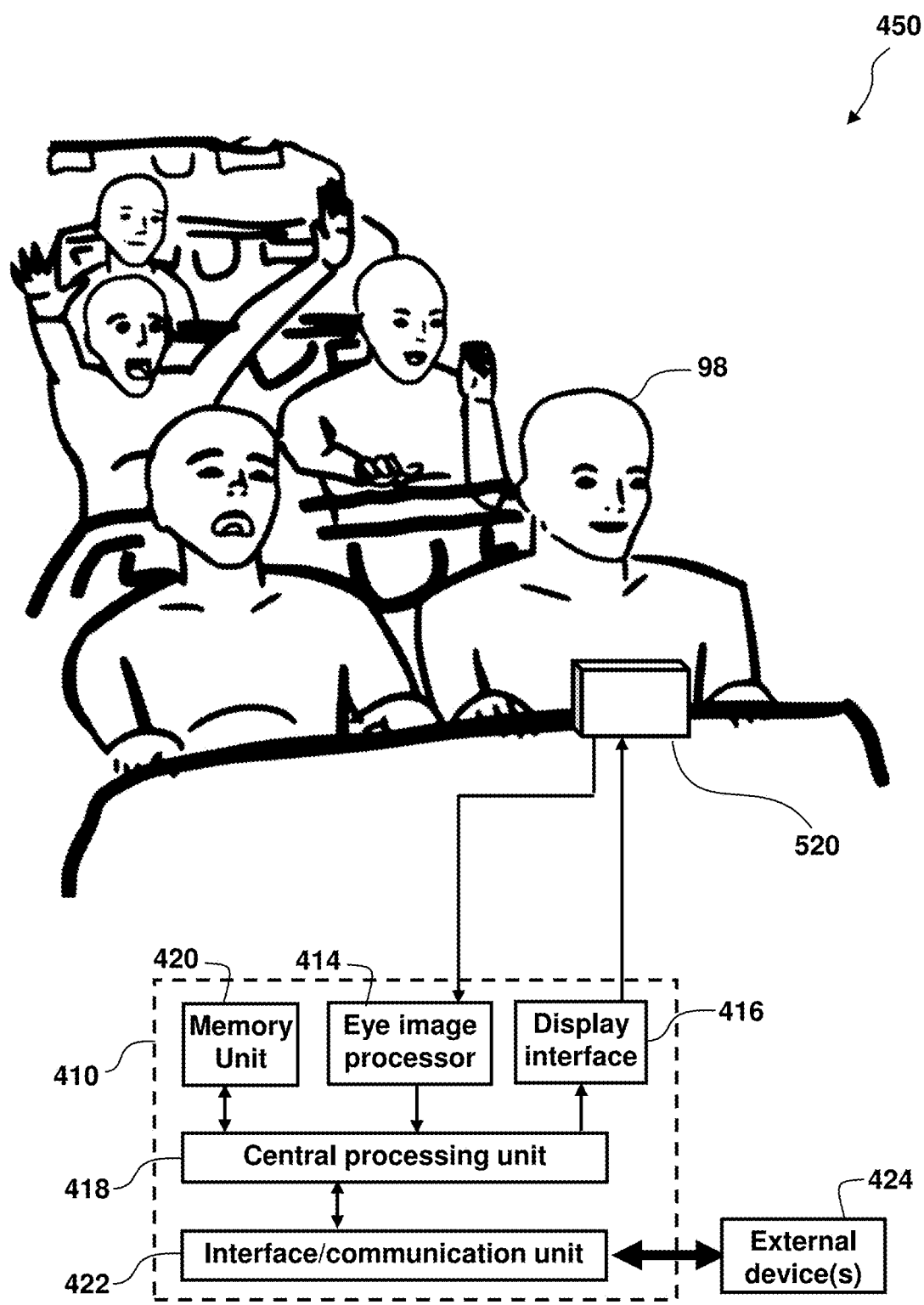
FIG. 18 is a mobile device system to assess health in a provocative environment.

FIG. 18 shows a system that uses a mobile device, such as the cellphone shown at 520 to assess human health in a provocative environment. In this case, the system 450, is being used to test a human subject 98 on a roller coaster. Testing can be performed using a cellphone 520 that displays a target. This scene, in this case, is not displayed. Instead, it is the surrounding provocative environment. In this system 450, the cellphone 520 also comprises the external eye imaging module, which would typically be a cellphone camera. In another embodiment, a mobile device, such as the cellphone providing a visual target could be used to assess human health in normal surroundings.

Referring to FIG. 16, FIG. 17, and FIG. 18, information from the external eye sensor 407 is received by an eye image processor 414 in an electronic module 410. Instructions on what to present are prepared by a display interface 416 in the electronic module and sent to the external display, which could be on a cellphone 520, it could be a three-dimensional display 432, or it could be an immersive two-dimensional display 430. Information for the eye image processor 414 and display interface 416 can be processed by a central processing unit 418, which can communicate with a memory unit 420 and an interface/communication unit 422 for transmission to an external device or devices 424.

Note that the display in any of the embodiments discussed herein could either have a visual target in a known location, or there could be some device to view and identify the location of the visual target. A forward-facing camera could be used to determine the location of the visual target in order to measure gaze and eye fixation. The forward-facing camera could be configured to capture images or video of the user's surroundings. Computer-vision algorithms can identify and locate objects within a scene. The forward-facing camera can provide information about the location of the target that can then be compared to the user's gaze direction. The user's gaze direction could be determined by an eye imaging module that images an eye component to measure and record eye orientation information. By combining information from both sources (e.g., the eye imaging module and the forward-facing camera) the user's ocular parameters can be determined. Machine learning models can be trained to associate patterns in the visual scene with specific visual targets.

Further Embodiments

In this document and other embodiments, the system for assessing a human health condition discussed herein can be comprised of artificial intelligence (AI) or train a machine learning-based model used for detecting the eyelid position based on the eye surface characteristic reflections, extracting eyelid positions by analyzing the images (image-based positions), generating data points based on the image-based positions; generating digital values based on the reflections; and providing the data points and digital values to train the machine learning based model for detecting the eyelid position based on the eye surface reflections. Quantum computing can also be used for processing and analyzing visual information. Quantum computing algorithms could be used to enhance image recognition and processing tasks relevant to eye tracking applications. Quantum machine learning algorithms could be applied to eye-tracking data for improved pattern recognition and analysis, helping in areas such as gaze prediction and understanding visual attention.

In another embodiment, the discussed system above can also comprise a forward-facing camera, configured to transmit video information, and which can communicate with the electronic circuit, and eye imaging sensors. This can be used to determine location of gaze, identify and correct slippage offsets of the extended reality device.

In another embodiment, the forward-facing camera with light sensor can calculate the ambient light level and then adjust the amount of light (e.g., brightness or dimness) entering the eye, which can be used for a measurement of ocular parameters, such as pupil size.

In another embodiment, the system described can be comprised of physiologic and biochemical sensors, which are in contact with the skin to provide biochemical and physiologic information from the body, which can communicate with the electronic circuit, eye sensors, body sensors and the recorded data from the physiologic and biochemical sensors can be correlated with the ocular parameter measures.

In an embodiment, the present invention can be comprised of an extended reality device which uses eye and head rotation information to measure ocular parameters to assess human health. The eye information can be acquired from an eye sensor that is comprised of at least one opto-electric transducer configured for converting a light signal to an electrical signal and information can be acquired from the head rotation sensor. The head rotation sensor and eye imaging sensor(s) can be integrated into an extended reality device. The system described is configured for measuring the position and movement responses of the eyes and head.

In the embodiments discussed herein, features include a forward-facing camera, eye imaging device, head rotation sensor controlled by an electronic circuit. Components of the electronic circuit can be activated or controlled haptically, auditorily, remotely, wirelessly, with gestures or movement of the eyes, head, hands or manually with a power switch on the device. Additionally, a bone or air conducting sensor can be incorporated in the framework of the device which can provide auditory/acoustic signals to issue an input signal to a controller to operate the system. The electronic circuit can also be activated by placing the extended reality device on the head which can issue a similar input signal when in contact with the skin and when removed from the head, the system will automatically become deactivated.

In an embodiment of the device, the system may include the user interface for providing information to the user of the device. The user interface may be associated with a touchpad, a keypad, buttons, a microphone, a haptic device, and/or other peripheral input devices. The processor may control functions of the system based on input received through the user interface. The system and/or testing function controls and input connections can be in the extended reality device and/or in a remote device. The computing system could be a distributed computing system. The computing system could comprise cloud computing. The ocular parameter measure methods can be comprised of an application connected to a cloud-based artificial intelligence infrastructure. The application can be made up of a series of tasks, and a user's eye movement can be recorded in data sets called Eye Movement Biomarkers (EMBs) and Gaze Mapping.

In one embodiment, the extended reality (XR) device or method can present a visual target to one eye (monocular) or both eyes (binocular). A power source can be attached to the XR device, and which can be rechargeable by a wireless interface.

In another embodiment, the extended reality device described herein can measure information between position and orientation of the head and eye position, and/or movement and/or eye reflexes and the ocular parameter being assessed. The data acquired can be processed by the face protection equipment and displayed to the user or collected data can be transmitted wirelessly to a smart phone, electronic device, or other computer source for the processing and viewing.

In an embodiment, the extended reality device can include an eye imaging and measuring system, a connected head rotation and measuring system, a power supply, a microprocessor, a memory, and a user interface. Components of the system may be configured to work in an interconnected fashion with each other and/or with other components coupled to respective systems. For example, the power supply may provide power to all the components of the system. The processor may receive information from all the affixed sensors and control the eye imaging system and the body rotation or orientation system.

In another embodiment, an extended reality device can have a manual control operating switch with an active and inactive mode. It can be comprised of an imaging device, a head rotation sensor, physiologic sensors, biochemical sensors, and an electronic circuit comprising a central processing unit with memory unit. Collected data can be transmitted to a small electronic device where easily understandable results can be seen.

In another embodiment, a mental health condition can be assessed by an abnormal ocular parameter and/or an abnormal mental health function assessment from a group of cognitive assessment tools including attention, navigation, perception, and search assessments.

In an embodiment, cognitive training and/or cognitive feedback can be performed and measured by comparing the eye position and/or movement between each eye, between the position and/or movement of the eyes and between the position and/or movement of a natural scene target and eyes.

In embodiments of the invention, the imaging device can comprise components configured to provide images of eye position and eye movement using components of the eye. The components can include a light source, diffracting elements to alter the light source, and opto-electric transducer configured for converting the light signal to an electrical signal. Both imaging device and head rotation sensor components can be electrically coupled such that eye information can be compared to head rotation signals with ocular parameter measurements.

In an embodiment, ocular parameter measurements can provide an indicator of the response to a pharmacologic therapeutic intervention.

In another embodiment, ocular parameter measurements can provide a neurologic, or physiologic indicator of a response to a therapeutic intervention.

In another embodiment, saccadometry and specifically prosaccade and antisaccade measures can be used to detect behavioral health conditions, mental health conditions, and neurologic conditions.

In an embodiment, vergence can be measured and compared in both eyes, as the visual target in the subject's visual field appears to move forward and away from the individual's eyes. This movement of the visual target can be a continuous transition, or it can occur in a series of distinct stages. Poor vergence performance can be recorded, indicating abnormal changes of accuracy, convergence, divergence, peak velocity, amplitude, symmetry, or latency, and can be used to determine neurologic conditions, such as TBI, biochemical impairments such as metabolic dysfunction, as well as physiologic impairments such as fatigue or intracranial fluid pressure impairment.

In another embodiment, vergence can be measured during continuous transition of different depths vertically, horizontally, or diagonally as the visual target gets closer or further from the user's eyes combined with dynamic motion of the head, which is moving in the same pattern or direction as the visual target.

In another embodiment, assessment of vergence dysfunction is performed for detection and/or quantification of acute traumatic brain injury, and/or recovery and is comprised of disconjugate movement of the eyes to track objects varying in depth over the visual field.

In another embodiment, saccades can also be measured using the extended reality device as discussed in this document, during other ocular parameter measures including vergence, head static smooth pursuit, and vestibular ocular reflex (VOR), vestibular ocular reflex suppression (VORS). The occurrence of saccades, saccadic intrusions, or saccade dynamics on fixational eye movement during ocular parameter measure can be related to neurologic conditions or impairments of human health.

In another embodiment, head static smooth pursuit can be measured while the head remains stable, and the eyes are focused on a visual target that moves in various directions. An abnormal head static smooth pursuit performance can be indicated by abnormally measured eye movement and/or eye position and/or eye orientation changes of gain (peak velocity/target velocity), velocity changes, accuracy of following a moving object or latency. These abnormalities can assess neurologic conditions like TBI, physiologic impairments such as fatigue and biochemical impairments due to hormone or electrolyte abnormalities.

In an embodiment, pupil performance can be measured by determining pupil size for at least one eye, while a user views stationary alternating bright and dim targets seen in the visual field. Alternatively in another embodiment, these visual targets, having varied light intensities, can be moving toward or away from the eye, or they can be presented in different positions with different characteristics, requiring the subject to recognize the difference between the visual targets. Poor pupil performance can include abnormal measures of pupil size, dilation information of acceleration, amplitude, latency or duration, and constriction information of amplitude, latency, or duration. These abnormal pupil measures can detect neurologic conditions like concussions, biochemical impairments with metabolic dysfunction, and physiologic impairment with cardiac disease, such as hypotension.

In an embodiment, eyelid performance can be measured and compared between each eye with a visual stimulus, at various intensities of brightness, with varied task content and at varying speeds causing eyeblinks. Abnormal eyelid performance can be associated with abnormal velocity of eyeblinks, duration of eyeblinks, amplitude or frequency of eyeblinks which can detect the presence of neurologic conditions, such as concussions, biochemical impairments associated with electrolyte or metabolic dysfunction and physiologic impairments which occurs with fatigue, or lack of alertness.

In another embodiment, a concussion can be detected by viewing a visual stimulus and capturing eyeblink raw data from at least of one eye of the subject in response to the visual stimulus, using an eye imaging device and analyzing eyeblink frequency.

In an embodiment, a concussion can be detected by viewing a visual stimulus and capturing eyeblink raw data from both eyes of the subject in response to the visual stimulus using an eye imaging device and analyzing the number of blinks in one eye of the subject that does not have a corresponding blink frequency rate in the other eye of the subject.

In another embodiment, anyone of the ocular parameter measurements discussed in this document can be used to assess the condition of human health and implemented for training athletes or other individuals in their occupational activities, to assume a supernormal level of performance.

In another embodiment, the extended reality (XR) device can be configured for use with machine learning such that a classifier can recognize any abnormal ocular parameter measured and provide classification of raw gaze datasets, belonging to eye fixations, saccades, or other predetermined categories. The classified algorithm or quantum algorithm can be used to assess whether the data can be used for training or specific visual rehabilitation, based on the abnormal datasets, and can modify an attribute of the training or visual rehabilitation according to the measured ocular parameters.

In an embodiment, the extended reality systems discussed herein can be portable, autonomous, constantly sensing head and eye information with the use of an artificial intelligence (AI) program, or quantum computing algorithms, and/or classifiers to assess the human health condition and can provide this information to the user as well as wirelessly transmit this information to a remote electronic device.

In an alternative embodiment, the present invention can visually rehabilitate or retrain the user when a specific ocular parameter abnormality is present. Visual-oculomotor-vestibular (VOV) rehabilitation can enhance ocular parameter visual accuracy with specific visual stimulation and body movements. VOV rehabilitation can help a user of the device improve the health conditions or impairments by exercising, enhancing, and/or retraining the abnormally detected ocular parameter. This type of rehabilitation system can also provide more rapid recovery of an abnormal ocular parameter by visually stimulating the associated neurologic pathway and connections affected by the neurologic, physiologic, or biochemical impairments with repetitive ocular parameter techniques.

In another embodiment, ocular parameter assessment can be used to train the oculomotor system and brain with individualized program, which can increase accuracy of eye fixation, cognition, attention, reaction time, fatigue, and treat traumatic brain injuries and mental health impairments.

In an embodiment, mental health assessment and/or training can be performed with an eye imaging device which measures the right and left eye movement, and/or eye gaze positions, and/or eye orientation during the time a viewed object is moving on a display and measured. Disconjugate measurement between the eyes is compared to detect an oculomotor impairment. A report can be provided if a disconjugate measure is present, indicating the presence of an oculomotor impairment and/or mental health condition. Disconjugate measures can also be used for training to improve a mental health condition or oculomotor impairment.

Alternatively, in another embodiment, mental health assessment or behavioral health assessment can be performed with an eye imaging device to measure eye movement, and/or eye gaze position, and/or eye orientation. A measured analysis can be generated from the eye measurement information (e.g., eye movement, and/or eye gaze position, and/or eye orientation) of at least one eye can be compared to the position of the object observed by the user. Another measured analysis, representing a physiologic impairment and/or mental health condition analysis can be generated when there is a difference between eye measurement information and the position of the object viewed by the user.

In another embodiment, ocular parameter measurement can be used for assessment, management, and rehabilitation periodically to analyze mental health progress. A mental health rehabilitative program can be used to improve specific cognitive impairments. Mental health testing can also be used for assessing deployment or occupational activity readiness, situational awareness, predicting human performance, and stress management.

In another embodiment, an artificial intelligence health platform can be operable for autonomous operation using a variety of learning methods and/or predictive analytic techniques to assess the health conditions and/or need for rehabilitation and/or training. The artificial intelligence health platform, comprised of a plurality of different engines can assess neurologic conditions, mental health conditions, behavioral health conditions, physiologic impairments, biochemical impairments and determine human performance capability.

In another embodiment, artificial intelligence (AI) and machine learning can be used analyze the results of ocular parameter assessments, in tandem with visual mental health function assessments discussed herein, patient records and reported symptoms, to diagnose the type and severity of mental health conditions.

In an embodiment, the information collected from ocular parameter measurement(s) of a user can be logged, stored, and transmitted to another data collection source.

In another embodiment, the collected eye and head movement data from ocular parameter measurements can use artificial intelligence and machine learning to detect health-related biomarkers related to detecting and diagnosing health conditions, such as CTE, with abnormalities of mental health function and behavior to automatically personalize VOV rehabilitation therapy plans. This VOV rehabilitation therapy can also access the software therapy from the cloud, through a smartphone, or other electronic device. Once the measured ocular parameters assess the health condition of the subject, the identity proofing, privacy, and security for the subject can be established. Information regarding normal ocular parameters and/or abnormal ocular parameters can be wirelessly transmitted to the cloud. Artificial intelligence and machine learning in the cloud can establish the rehabilitation program needed, based on the abnormal ocular parameter measured, or further training desired by the subject to obtain above normal performance with the selected parameter.

In another embodiment, the specific electronic prescription, determined by the computer code (machine learning algorithm) in the cloud or other external electronic device, can be transmitted to the trainer/rehabilitation therapist and/or to the subject or to others, such as providers of the subject's health care. Specific programming can also be accessed and actively streamed to the user automatically, upon sensing an abnormal parameter value associated with a particular impairment or the need for training of a specific parameter desired. The subject with normal parameters desiring training can select specific programs to enhance eye fixation with activities to super-normal levels. The subject having an abnormal ocular parameter(s) can be trained with specific visual ocular tasks to rehabilitate the ocular parameter(s) which was abnormal. Eye movement and/or eye position and/or eye orientation changes, pupil size and eyeblinks can be measured with the VOV rehabilitation tasks or with the visual training tasks. The improvements can be determined by the measured data and wirelessly transmitted back to the cloud for data logging.

In another embodiment, the eye imaging module affixed of an extended reality device can assess the retina for anatomic changes, such as with vessels or the optic disc, biochemical changes, such as with protein or lipid biomarkers, or physiologic changes, such as blood flow or cerebrospinal fluid changes, as biomarkers to detect a traumatic brain injury.

In an embodiment, data obtained from the extended reality device can be transmitted by wireless communication to a remote device. For exampled eye imaging or eye and head orientation could be pushed to a smart phone, an iPad or a computer.

In another embodiment, the raw data collected from the eye imaging sensor(s) and/or position sensor or eye imaging sensor(s) and/or position sensor and body movement sensor and/or position sensor is transmitted wirelessly, to an external source such as the cloud, or external device for further processing.

In another embodiment, the device as described herein, can be a mounted head mounted display system in a vehicle and the use of the display can be used to detect the health status of the operator, and if unhealthy can be used to control the vehicle.

Embodiments described herein can be used with a protective helmet including those designed for sport activities and/or industrial activities. Various embodiments can also be used for safety helmets, such as construction or industrial helmets, and helmets used by law enforcement, security and/or military forces.

Areas of Application

Sports. Embodiments of the invention(s) can be used in sport environments where ocular parameter measurement can help predict player performance, player fatigue, attention, cognition, and early detection of traumatic brain injury. Additionally, if an athlete had such an abnormality and could be given rehabilitation, this can correct the abnormality and allow the athlete to return to play activities sooner. Embodiments of the invention(s) can be used for TBI/concussion management, in which detection, quantification, and monitoring of concussions can be performed with the technology as well as determining when the athlete is safe to return to play, following a concussion, based on the eye movement responses. This technology can prevent the more serious recurrent concussions, especially if they are closely related to the previous concussion. Substance use impairment can also adversely affect ocular performance. Embodiments of the invention(s) can be used for impairment or performance screening and predict player performance based on eye fixation ability.

Medical. Embodiments of the present invention can be useful for centers that perform concussion detection/management, drug screening, employee assessment, pharmalogical assessment, detection/assessment for neurologic conditions, vestibular rehabilitation and athletic/vocational enhancement. Embodiments can be used specifically for cognitive impairment monitoring, mental health monitoring, behavioral health monitoring, neurologic health monitoring, monitoring eye disease, biochemical impairment monitoring, and physiologic impairment monitoring. Health monitoring with artificial intelligence (AI) with the technology discussed herein can collect, analyze, and interpret health-related data in real-time. AI algorithms or quantum algorithms can analyze historical health data to predict the likelihood of future health events. Early detection of health issues can allow for timely pharmaceutical or other types of intervention and preventive measures.

This invention can provide objective tools for early detection of health-related biomarkers for neurologic impairments, including traumatic brain injury (TBI), biochemical impairments or physiologic impairments which would affect the human health condition.

Although the invention herein has been described with reference to embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Further variations and modifications of the disclosed embodiments can also be used. The principles described here can also be used for applications other than sports. While the principles of the disclosure have been described above in connection with specific apparatuses and methods, it is understood that this description is made only by way of example and not as limitation on the scope of the disclosure.

What is claimed is:

1. A system for assessing a human health condition, wherein:
   the system comprises a wearable device;
   the wearable device comprises an eye imaging module and a display;
   the eye imaging module is configured for imaging an eye component wherein the eye component is selected from the group of:
   a retina;
   a sclera;
   a cornea;
   an iris;
   a limbus;
   a pupil; and
   an eyelid;
   the eye imaging module determines eye information in response to imaging the eye component at a plurality of times, wherein the eye information is selected from the group of:
   eye orientation information at a plurality of times;
   pupil size at a plurality of times; and
   eyelid position information at a plurality of times;
   the system further comprises an electronic circuit;
   the electronic circuit is responsive to the eye information to generate an ocular parameter measurement selected from the group of:
   a saccade measurement;
   a vestibular ocular reflex suppression measurement;
   a vergence measurement;
   a head static smooth pursuit measurement;
   a pupil size change measurement;
   an eyeblink measurement;
   a gaze measurement;
   a fixation measurement; and
   a vestibular ocular reflex measurement;
   the system is configured to assess a human health condition in response to the ocular parameter measurement from the electronic circuit; and the assessed human health condition is selected from the group of:
  normal human health:
  a neurologic condition;
  a mental health condition;
  a behavioral health condition;
  a biochemical health impairment; and
  a physiologic impairment.

2. The system of claim 1, wherein:
the assessed human health condition comprises a neurologic condition; and
the neurologic condition comprises a traumatic brain injury.

3. The system of claim 2, wherein:
the eye imaging module comprises a first module for imaging a left eye and a second module for imaging a right eye; and
the first module and the second module each comprise an infrared light source, a prism or mirror, and a photodetector.

4. The system of claim 3, wherein:
the display is configured to present a training protocol to a user;
the eye imaging module is configured to measure and record eye information that is responsive to the user's response to the training protocol; and
the training protocol is responsive to the recorded eye information.

5. The system of claim 1, wherein:
the assessed human health condition comprises a mental health condition;
the mental health condition comprises a cognitive impairment;
the system is further configured to diagnose the cognitive impairment in response to health-related biomarkers that are detected in response to a detected abnormal ocular parameter;
the abnormal ocular parameter is detected in response to:
  the ocular parameter measurement from the electronic circuit; and
  baseline values of ocular parameter measurements.

6. The system of claim 1 wherein:
the assessed human health condition comprises a condition selected from the group of:
  a neurologic condition;
  a biochemical impairment; and
  a physiologic impairment; and
the system is configured for assessing a pharmacologic intervention in response to the assessed human health condition.

7. The system of claim 6 wherein:
the assessed human health condition comprises a neurologic condition; and
the neurologic condition comprises an impairment selected from the group of:
  a traumatic brain injury;
  a neurocognitive impairment;
  a cerebral inflammatory impairment;
  an autoimmune impairment;
  a cerebrovascular impairment;
  a seizure impairment;
  a neuromuscular impairment;
  a neurogenetic impairment;
  a neurodegenerative impairment; and
  a neoplastic impairment.

8. The system of claim 1, wherein:
the eye component comprises an eyelid;
the eye information comprises eyelid position at a plurality of times;
the ocular parameter measurement comprises eyeblinks;
the assessed human health condition comprises a physiologic impairment; and
the assessed human health condition is used as input for control of an external system.

9. The system of claim 1, wherein:
the assessed human health condition comprises a biochemical impairment;
the biochemical impairment comprises a metabolic dysfunction; and
the metabolic dysfunction comprises a hormonal abnormality.

10. The system of claim 1, wherein:
the system is configured to determine an abnormal ocular parameter; and
the abnormal ocular parameter is used to detect a health-related biomarker using an additional input selected from the group of health history and physical exam information to assess an abnormal health condition.

11. The system of claim 1, wherein:
the system is configured to diagnose a mental health condition;
the mental health condition comprises cognitive impairment.

12. The system of claim 1, wherein:
the ocular parameter measurement comprises is used to detect a biomarker;
the assessed human health condition comprises a neurologic condition; and
the neurologic condition comprises a cerebrovascular impairment selected from the group of:
  a migraine;
  a stroke;
  a transient ischemic attack;
  vascular dementia;
  cerebrovascular stenosis; and
  a cerebrovascular aneurysm.

13. The system of claim 1, wherein:
the system is further configured to diagnose the human health condition in response to health-related biomarkers that are detected in response to:
  a detected abnormal ocular parameter;
  an additional input selected from the group of:
    health history; and
    physical examination information; and
the abnormal ocular parameter is detected in response to:
  the ocular parameter measurement from the electronic circuit; and
  baseline values of ocular parameter measurements.

14. The system of claim 1, wherein:
the assessed human health condition comprises a behavioral health condition; and
the behavioral health condition comprises impairment from substance use.

15. The system of claim 1, wherein:
the assessed human health condition comprises an assessed physiologic impairment;
the training protocol is responsive to the assessed physiologic impairment.

16. A head-worn system for assessing human health, wherein:
the head-worn system comprises a head-worn eye imaging module configured for imaging an eye component;

the eye component is selected from the group of:
a retina;
a sclera;
a cornea;
an iris;
a limbus;
a pupil; and
an eyelid:
the head-worn eye imaging module is configured for imaging the eye component at a plurality of times to determine eye information selected from the group of:
eye orientation at a plurality of times;
pupil size at a plurality of times; and
eyelid position at a plurality of times;
the head-worn eye imaging module is further configured for transmitting the eye information to an electronic circuit that is configured for generating an ocular parameter measurement selected from the group of:
a saccade measurement;
a vestibular ocular reflex suppression measurement;
a vergence measurement;
a head static smooth pursuit measurement;
a pupil size change measurement;
an eyeblink measurement;
a gaze measurement;
a fixation measurement; and
a vestibular ocular reflex measurement;
the electronic circuit is further configured to assess a human health condition selected from the group of:
normal human health:
a neurologic condition;
a mental health condition;
a behavioral health condition;
a biochemical health impairment; and
a physiologic impairment.

17. The head-worn system of claim 16, wherein:
the head-worn system further comprises a head-worn display;
the display is configured to present a visual target; and
the system is configured for rehabilitation.

18. The head-worn system of claim 16, wherein:
the human health condition comprises a physiologic impairment; and
the physiologic condition comprises impairment from fatigue.

19. A method for assessing a human health condition, wherein:
the method comprises establishing an eye imaging module on a wearable device;
using the eye imaging module to image an eye component selected from the group of:
a retina;
a sclera;
a cornea;
an iris;
a limbus;
a pupil; and
an eyelid:
using the eye imaging module to image a human eye component at a plurality of times to determine eye information selected from the group of:
eye orientation at a plurality of times;
pupil size at a plurality of times; and
eyelid position at a plurality of times; and
transmitting the eye information to an electronic circuit;
using the electronic circuit to generate an ocular parameter measurement selected from the group of:
a saccade measurement;
a vestibular ocular reflex suppression measurement;
a vergence measurement;
a head static smooth pursuit measurement;
a pupil size change measurement;
an eyeblink measurement;
a gaze measurement;
a fixation measurement; and
a vestibular ocular reflex measurement;
assessing the human health condition in response to the ocular parameter measurement, wherein the human health condition is selected from the group of:
normal human health:
a neurologic condition;
a mental health condition;
a behavioral health condition;
a biochemical health impairment; and
a physiologic impairment.

20. The method for assessing the human health condition of claim 19, wherein:
the human health condition comprises a neurologic condition; and
the system is further configured to assess the effectiveness of a pharmacological intervention.

* * * * *